United States Patent
Nirmalan et al.

(10) Patent No.: US 6,422,743 B1
(45) Date of Patent: Jul. 23, 2002

(54) METHOD FOR DETERMINING HEAT TRANSFER PERFORMANCE OF AN INTERNALLY COOLED STRUCTURE

(75) Inventors: Nirm V. Nirmalan, Niskauna, NY (US); Jeffery F. Rhodes, Zionsville, IN (US)

(73) Assignee: Allison Advanced Development Company, Indianapolis, IN (US)

( * ) Notice: Subject to any disclaimer, the term of this patent is extended or adjusted under 35 U.S.C. 154(b) by 0 days.

(21) Appl. No.: 09/535,468

(22) Filed: Mar. 26, 2000

(Under 37 CFR 1.47)

Related U.S. Application Data

(60) Provisional application No. 60/126,564, filed on Mar. 26, 1999.

(51) Int. Cl.7 .......................... G01N 25/20; G01K 17/00
(52) U.S. Cl. .............................. 374/43; 374/25; 250/330
(58) Field of Search ........................... 374/4, 5, 43, 44, 374/6, 7, 29; 250/330, 341.6

(56) References Cited

U.S. PATENT DOCUMENTS

| | | | |
|---|---|---|---|
| 3,566,669 A | * 3/1971 | Lawrence et al. | 374/179 |
| 4,644,162 A | * 2/1987 | Bantel et al. | 374/5 |
| 4,817,623 A | 4/1989 | Stoddart et al. | |
| 4,916,715 A | * 4/1990 | Adiutori | 374/29 |
| 4,983,836 A | * 1/1991 | Matoba et al. | 250/330 |
| 5,111,046 A | * 5/1992 | Bantel | 250/330 |
| 5,168,161 A | * 12/1992 | Markandey | 250/330 |
| 5,231,287 A | 7/1993 | Sekine et al. | |
| 5,321,290 A | 6/1994 | Dean et al. | |
| 5,335,993 A | 8/1994 | Marcus et al. | |
| 5,376,793 A | * 12/1994 | Lesniak | 250/341.8 |
| 5,386,117 A | 1/1995 | Piety et al. | |
| 5,396,068 A | 3/1995 | Bethea | |
| 5,709,469 A | 1/1998 | White et al. | |
| 5,711,603 A | * 1/1998 | Ringermacher et al. | 374/5 |
| 5,756,878 A | 5/1998 | Muto et al. | |
| 5,883,388 A | 3/1999 | Smith et al. | |

FOREIGN PATENT DOCUMENTS

| | | | | |
|---|---|---|---|---|
| DE | 3407911 | * | 9/1985 | 250/338.1 |

OTHER PUBLICATIONS

Tresek et al. Provocative techniques in Thermal NDT Imaging. Presented at the National Spring Conference of the american society for NDT, Mar. 1975.*

Pollack. Advances in Turbine Temperature Measurements. Proceedings of the 22nd international Symposium. san Diego, CA, May 1976.*

* cited by examiner

*Primary Examiner*—Diego Gutierrez
*Assistant Examiner*—Gail Verbitsky
(74) *Attorney, Agent, or Firm*—Woodard, Emhardt, Naughton Moriarty & McNett

(57) ABSTRACT

A method by which the heat transfer quality of a cooled gas engine component can be quantified for inspection purposes. A system is utilized to determine the heat transfer performance of an internally cooled structure, by analyzing the transient thermal response of the structure based upon a full field surface temperature measurement using an infrared thermal imaging system.

18 Claims, 7 Drawing Sheets

METHOD FOR DETERMINING HEAT TRANSFER PERFORMANCE OF AN INTERNALLY COOLED STRUCTURE

The present application claims the benefit of U.S. Provisional Application No. 60/126,564 filed Mar. 26, 1999, which is incorporated herein by reference.

BACKGROUND OF THE INVENTION

The present invention relates generally to a method by which the heat transfer quality of a cooled gas turbine engine component can be quantified for inspection purposes. More particularly, in one embodiment the present invention determines the heat transfer performance of an internally cooled structure by analyzing the transient thermal response of the structure based upon a full field surface temperature measurement using an infrared thermal imaging system. Although the present invention was developed for use in association with gas turbine engine components, certain applications may be outside of this field.

A gas turbine engine conventionally comprises a compressor for compressing air to the proper pressure required for supporting the combustion of fuel in a combustion chamber. The high temperature gas exiting the combustion chamber provides the working fluid for the turbine, which powers the compressor. The turbine, which is driven by the flow of high temperature gas, is utilized to turn a propeller, fan or other device. Further, the high temperature gas may be used directly as a thrust for providing motive power, such as in a turbine jet engine.

It is well known that the performance of a gas turbine engine increases with the increase in the operating temperature of the high temperature gas exiting the combustion chamber. A factor limiting the allowable temperature of the gaseous working flow from the combustion chamber is the capability of the various engine components to not degrade when exposed to the high temperature gas flow. Engine designers to cool the engine components in order to increase the upper limit on the operating temperature of the gaseous working fluid have utilized various techniques. A conventional technique that engine designers have used to allow the use of higher temperature working gases is an internal network of apertures and passageways within the component. A steady flow of pressurized cooling media is passed through the internal passageways of the component, and the cooling media is finally exhausted onto the exterior surface of the component. The passage of the cooling media through the internal passageways and out through the exit aperture provides for convective heat transfer from the walls of the component to the cooling media.

Cooling of the components of the gas turbine engine is preferably accomplished with a minimum amount of cooling media, since the cooling media is working fluid, which has been extracted from the compressor, and its loss from the gas flow rapidly reduces engine efficiency. The engine designer must design an engine to operate within a specified temperature range, while minimizing the amount of cooling media extracted from the compressor. If these design parameters are not satisfied, a corresponding structural degradation of the engine components may result, or the efficiency of the engine may be reduced because an excessive quantity of cooling media was extracted from the compressor.

Over the years, a number of techniques have been developed to inspect the cooling quality of gas turbine components. These techniques include (1) total, regional, or hole-by-hole airflow measurement; (2) water flow visualization; (3) ammonia/blueprint paper; and, (4) various less sophisticated thermal imaging techniques. The prior techniques are not able to detect internal flow characteristics and/or internal flow anomalies. Further, technique (1) is time consuming and techniques (2)–(4) are non-quantitative in nature.

Although the prior techniques are steps in the right direction for inspecting the cooling quality of gas turbine components exposed to high temperature gases, the need for additional improvement still remains. The present invention satisfies this need in a novel and unobvious way.

SUMMARY OF THE INVENTION

One form of the present invention is a technique to evaluate thermal response of an internally cooled structure. This technique includes determining one or more heat transfer characteristics of the structure.

In a further form of the present invention, evaluation data is provided by observing temperature changes over time at each of a number of locations along a structure. The evaluation data corresponds to a convective heat transfer coefficient estimated for each of the locations. The evaluation data may be used to assess the quality of parts by comparing the data to a known standard, to analyze initial thermal behavior of a new device configuration, or to direct repairs or maintenance, to name just a few applications.

In another form of the present invention, data is obtained by an infrared thermal imaging system observing temperature changes over time at each of a number of locations along the surface of a component that is being tested at near ambient conditions. The data is processed to separate the heat transfer associated with convection from conduction for the component at near ambient conditions.

One object of the present invention is to provide a unique method for determining the heat transfer performance for an internally cooled structure.

Related objects and advantages of the present invention will be apparent from the following description.

DESCRIPTION OF THE PREFERRED EMBODIMENTS

Figure 1:
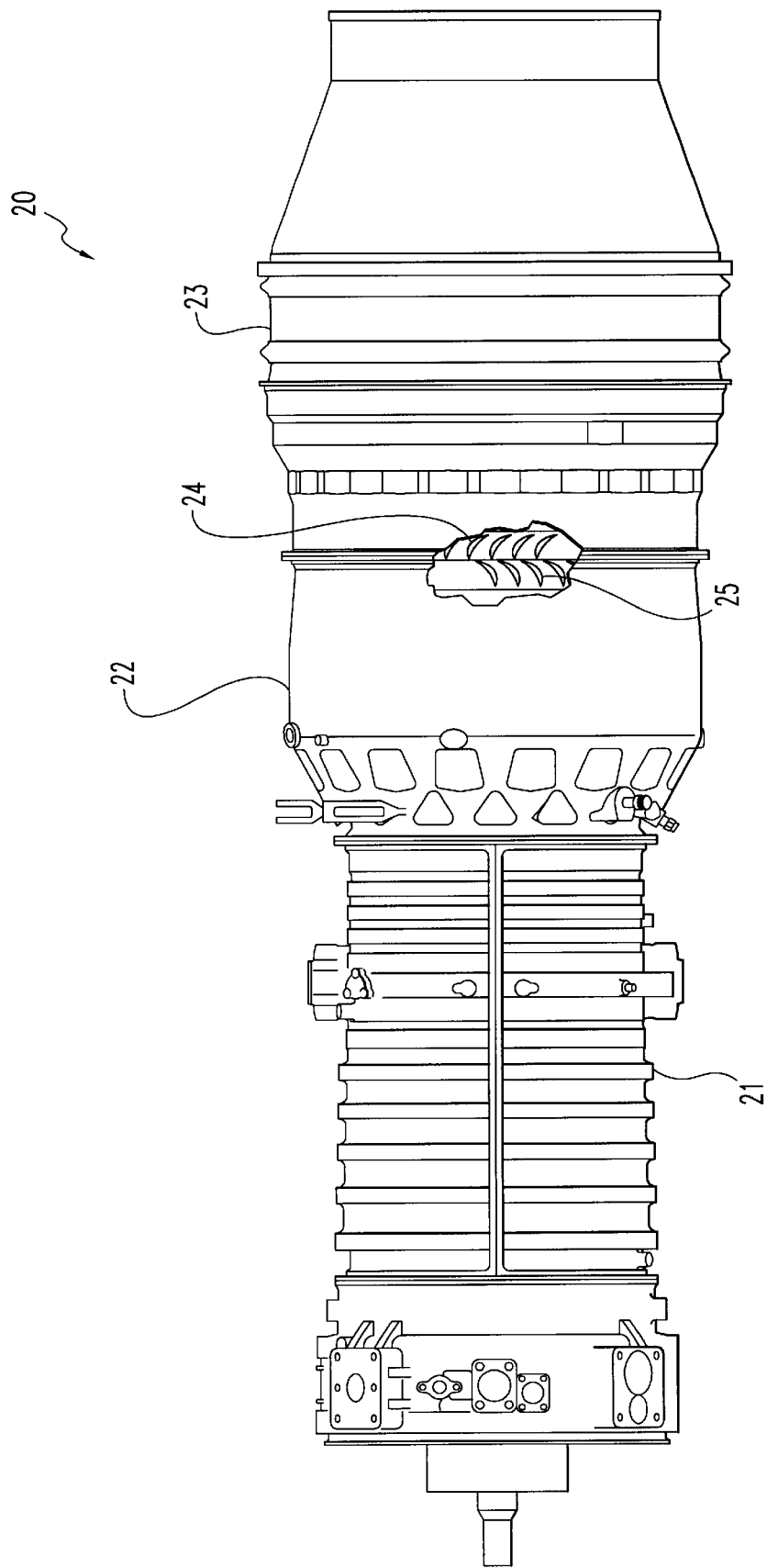
FIG. 1 is a partially fragmented perspective view of a typical gas turbine engine.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring to FIG. 1, there is illustrated a gas turbine engine 20 which includes a compressor 21, a combustor 22 and a power turbine 23. The three components have been integrated together to produce an aircraft flight propulsion engine. The term aircraft is generic and includes helicopters, airplanes, missiles, unmanned space devices and any other substantially similar devices. It is important to realize that there are a multitude of ways in which the gas turbine engine components can be linked together. Additional compressors and turbines could be added with intercoolers connecting between the compressors and reheat combustion chambers could be added between the turbines.

Further, the gas turbine engine is equally suited to be used for an industrial application. Historically, there has been widespread application of industrial gas turbine engines, such as pumping sets for as and oil transmission lines, electricity generation and naval propulsion.

A plurality of turbine blades 24 are coupled to a rotor disk that is affixed to a shaft rotatable within the gas turbine engine 20. A plurality of vanes 25 are conventionally joined together to collectively form a complete 360-degree nozzle. It is understood herein that gas turbine engine blades and vanes are often referred to as airfoils, and hereinafter this application will refer to blades and/or vanes as airfoils, unless specifically stated otherwise in the text. Other common gas turbine engine components that could be tested utilizing the methods of the present invention include but are not limited to combustor liners, exhaust nozzles, exhaust liners, blade tip shrouds, vane shrouds and other actively cooled components. Further, the methods and system of the present invention are not limited to inspection of gas turbine engine components and could be used to assess any actively cooled component.

In one embodiment, the gas turbine engine airfoils are formed of a heat resistant superalloy composition. There are various types of superalloy compositions, such as but not limited to nickel based or cobalt based compositions, and the manufacturers of such compositions are generally known to those skilled in the art. Most superalloy compositions of interest are complicated mixtures of nickel, chromium, aluminum and other select elements. The airfoils may be of a unitary cast configuration, and/or an assembly of cast components, and/or an assembly of cast and wrought components. The airfoils may have an equiax, directionally solidified or a single crystal alloy structure. In one embodiment, the gas turbine engine airfoils 24 and 25 are of a cast single crystal single structure. Further, in alternate embodiments of the present invention the products are formed of a metallic material, or an intermetallic material or a ceramic material.

Figure 2:
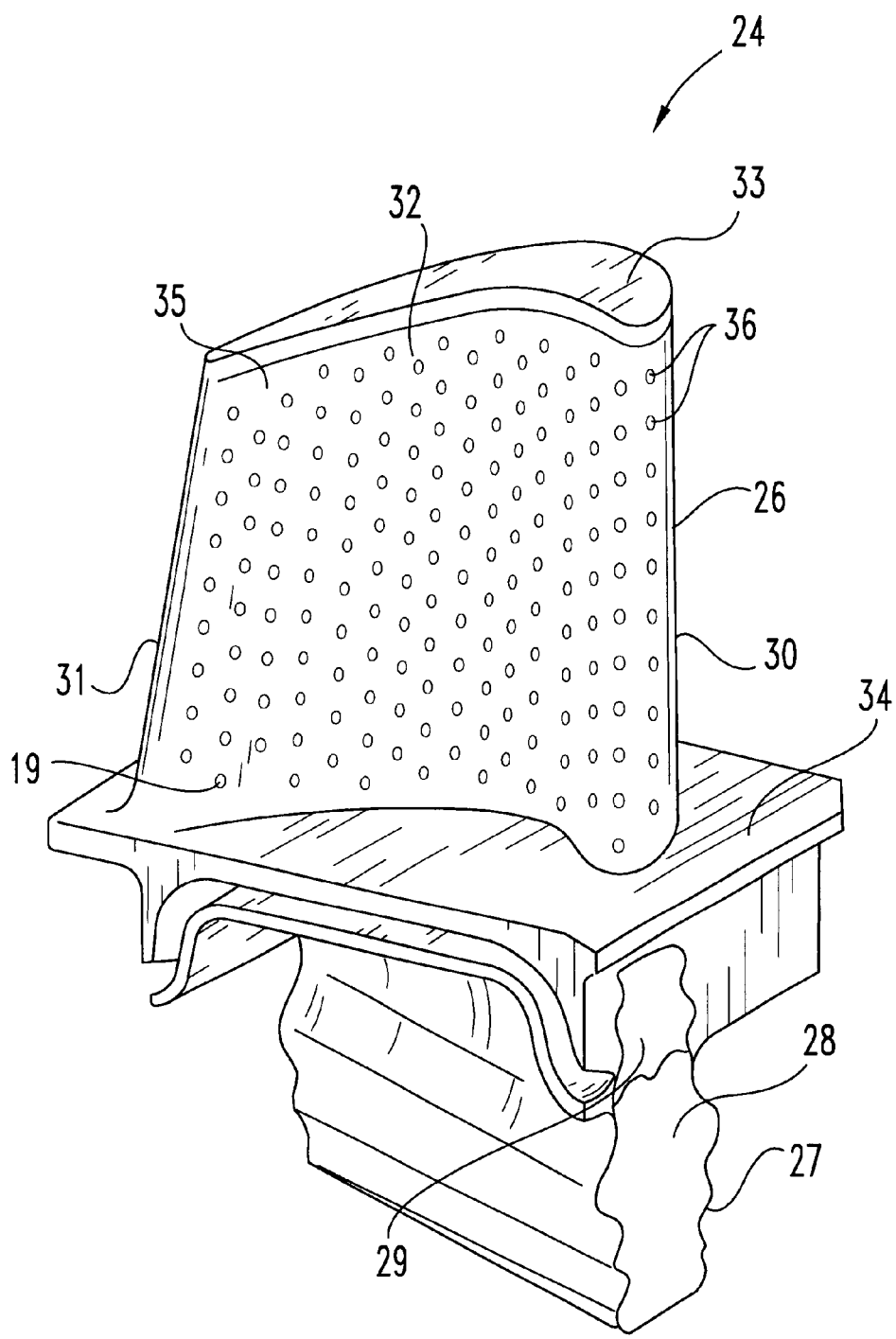
FIG. 2 is a perspective view of a blade comprising a portion of the FIG. 1 gas turbine engine.

With reference to FIG. 2, there is illustrated a perspective view of one embodiment of the gas turbine engine airfoil 24. The gas turbine engine airfoil has as principal regions an airfoil portion 26, a root portion 27 and a shank portion 28, which extends between the root portion 27, and the airfoil portion 26. The shank portion 28 has a central conduit 29 formed therein which is in fluid communication with a hollow cavity/passageway 30 (FIG. 3) within the airfoil 24. The hollow cavity 30 functions as an internal passageway for receiving cooling media from the compressor 21 and distributing it within the airfoil 24. The cooling media in the preferred environment is a compressible fluid such as air.

The airfoil 24 has a leading edge 30, a trailing edge 31, and an outer surface 32 extending therebetween. Hereinafter, the term spanwise will indicate an orientation between a tip 33 and a platform 34; and the term streamwise will indicate an orientation between the leading edge 30 and the trailing edge 31. The leading edge 30 faces in an upstream direction with respect to the approaching fluid flow and the trailing edge 31 faces in a downstream direction. The airfoil 24 includes a concave pressure side 35 and an opposite convex suction side (not illustrated). Arranged along the outer surface 32 of the airfoil 24 are a plurality of cooling media exit openings that allow for the discharge of cooling media across the outer surface. In one embodiment the cooling scheme includes: a plurality of exit apertures 36 spaced along the leading edge 26; a plurality of spaced discharge holes 37 spaced along a portion of the pressure side 35 of the airfoil; and a plurality of cooling apertures 19 spaced along a portion of the pressure side of the airfoil towards the trailing edge 31. However, other exit opening configurations are contemplated herein. It is understood that the blade 24 illustrated in FIG. 2 is not intended to be limiting and other cooling designs are contemplated herein.

Figure 3:
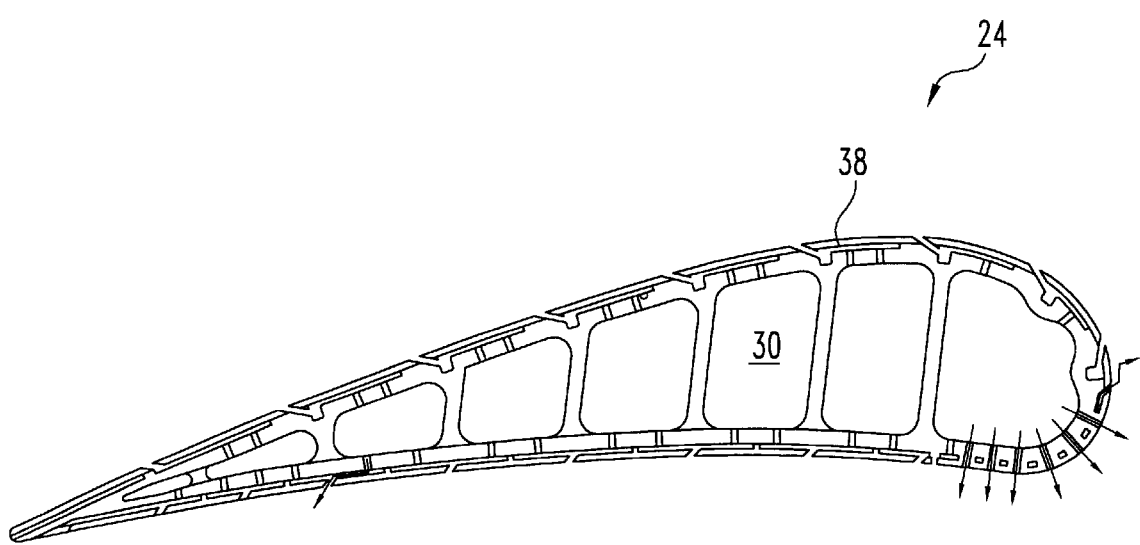
FIG. 3 is an illustrative view of one embodiment of a cooling system within a gas turbine blade.

With reference to FIG. 3, there is illustrated a sectional view of the airfoil 24. Airfoil 24 has it's passageway 30 extending therethrough for the delivery of cooling media to at least one cooling passageway 38 that is positioned adjacent the perimeter of the airfoil 24. In another preferred form of the present invention there are a plurality of cooling passageways 38 positioned around the perimeter of the airfoil 24. An outer surface 32 of the airfoil 24 is adapted for receiving a high temperature working fluid thereon. For clarity in illustration the sectional view of airfoil 24 of FIG. 3, has had the plurality of cooling pedestals removed. However, it is understood that there are in at least one embodiment of the present invention cooling pedestals within the cooling passageways 38. Further, alternate embodiments are contemplated herein where there are no cooling pedestals located within the cooling passageways 38. A plurality of apertures 40 are formed through the spar member 41 to allow the release of cooling media into the plurality of cooling passageways 38.

Figure 4:
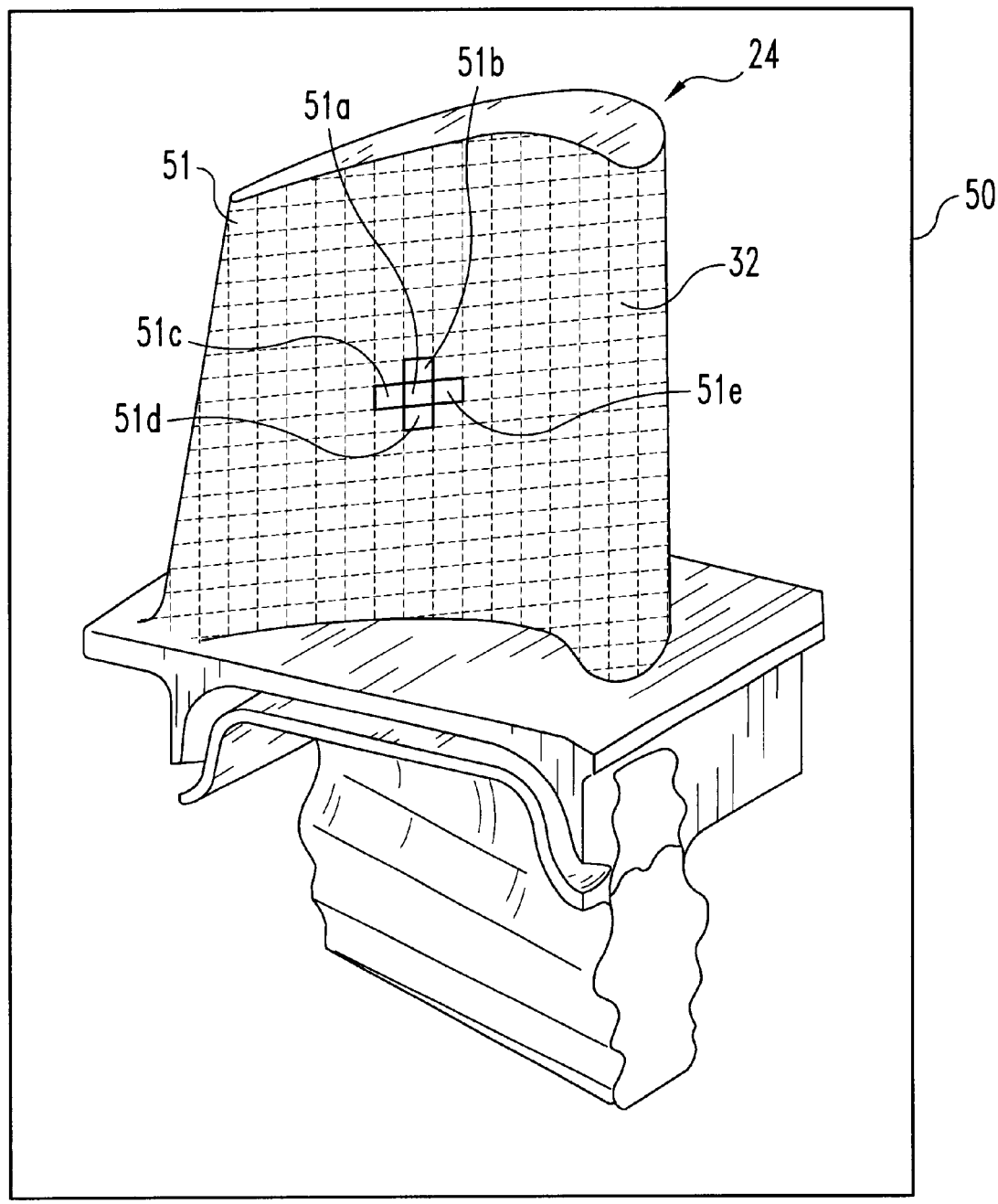
FIG. 4 is an illustrative view of a gas turbine engine blade within a thermal imaging system.

With reference to FIG. 4, there is illustrated the airfoil 24 within the field of view of an infrared thermal imaging system 50. The present invention will be illustrated and described with reference to the airfoil 24. However the techniques, methods and/or systems of the present invention are not limited to assessing a gas turbine engine airfoil, and as discussed previously are applicable to use with other components such as but not limited to combustor liners, exhaust nozzles, exhaust liners, blade tip shrouds, vane shrouds and other actively cooled components. Further, the methods and system of the present invention are not limited to inspection of gas turbine engine components and could be used to assess any actively cooled component.

The infrared thermal imaging system 50 is utilized to observe and/or quantify the response of a structure to changes in temperature. The infrared thermal imaging system is capable of acquiring transient surface temperature data in a pixel format. The data is also stored in a binary digital format that can be extracted and converted into a (t, T, x, y) format. In one form the infrared thermal imaging system has an x, y, & z traversing system, hot and cold airflow capability and different thermal sequences such as a flash of heat flux, cold air or hot air can be requested for certain periods of time. More preferably the infrared thermal imaging device is a TIP System available from Bales Scientific, Inc. of Walnut Creek, Calif. However, other infrared thermal imaging devices are contemplated herein.

The structure is evaluated with the infrared thermal imaging system over changing temperature conditions, such as by heating the outer surface 32 of the structure and then flowing a cooling fluid through the internal cooling passages of the structure. Convection, conduction, or induction or combinations thereof can accomplish the heating. In one form of the present invention the heating of the outer surface 32 is accomplished by flowing a hot fluid thereover. In one form the hot fluid and the cooling fluid are defined by air, however other fluids are contemplated herein. Data is collected by the infrared thermal imaging system which corresponds to the changes in temperature over time for a plurality of control volumes. In one form the infrared thermal imaging system is configured to provide the control volumes by a pixelated image of the structure. The plurality of pixels are represented in FIG. 4 as 51, and in one embodiment are within a range of about 0.010 to about 0.025 square inches, however other sizes are contemplated herein. Each pixel of the image corresponds to temperature at a different location along the structure, and the infrared thermal imaging system collects data for each of the pixels including x,y location, temperature and time.

The temperature differences across the surface are determined by comparing the pixel data of one location to the pixel data of another location. The temperature differences across the surface can be reflected graphically as differences in color or shading between the pixels, and/or the pixel data corresponding to the temperature differences as gathered by the infrared thermal imaging system may be used for evaluation of temperature differences without generating an image. In one form of the present invention the infrared thermal imaging system generates digital thermal data for each pixel that is used directly for evaluation of the heat transfer performance of the internally cooled structure.

Data corresponding to the change in temperature over time for each pixel of the structure is utilized to estimate one or more heat transfer characteristics. The heat transfer characteristic may then be used directly or subsequently manipulated to provide information useful in assessing the heat transfer quality of the structure. For example, an internal convective heat transfer coefficient (h) may be determined at each pixel location by modeling the thermal response in accordance with the present invention. Each pixel of data has the transient heat balance equation (1) applied as follows:

$$\rho C_p t_h \Delta x^2 \Delta T_{m,t}/\Delta t = h\Delta x^2(T_m-T_c)+k_m \Delta x t_h \Sigma(\Delta T_{m,x}/\Delta x) \quad (1)$$

Figure 5:
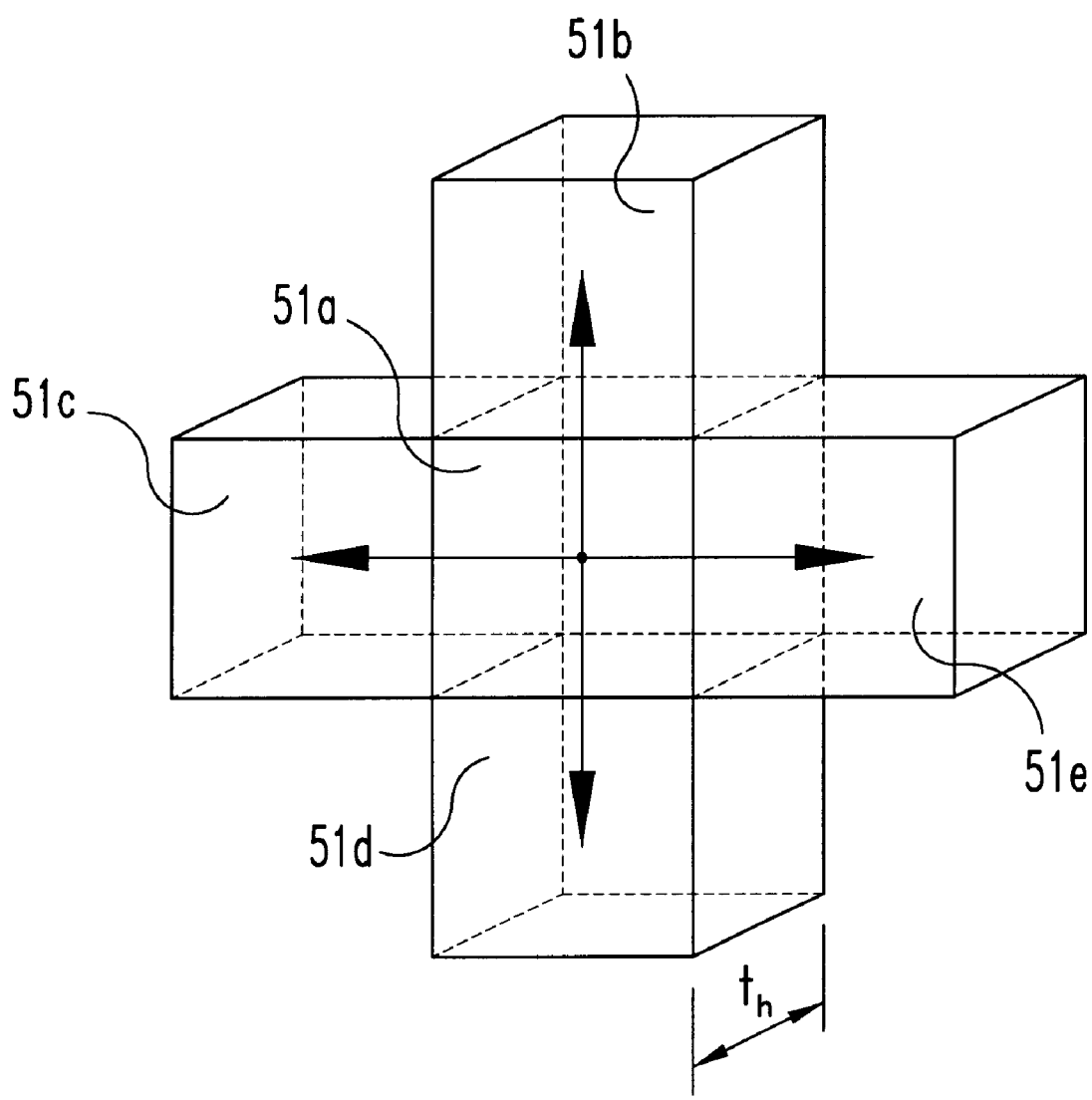
FIG. 5 is an enlarged partial perspective view of a portion of the surface of the gas turbine engine blade of FIG. 4, wherein the surface is broken into pixels of temperature data.
Figure 6A:
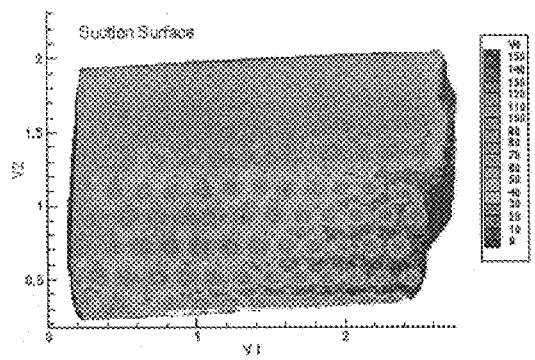
FIGS. 6A, 6B, 6C, and 6D (collectively FIG. 6) show graphic images of heat transfer coefficient contours or "maps" determined in accordance with the present invention of a cooled gas turbine engine blade.
Figure 6B:
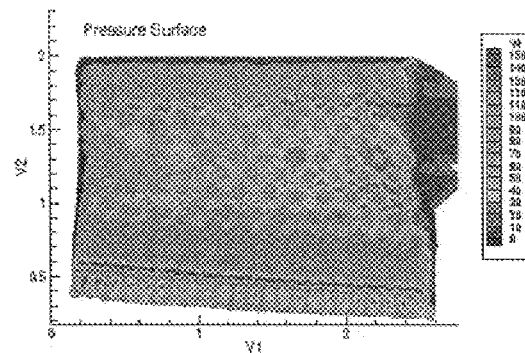
Figure 6C:
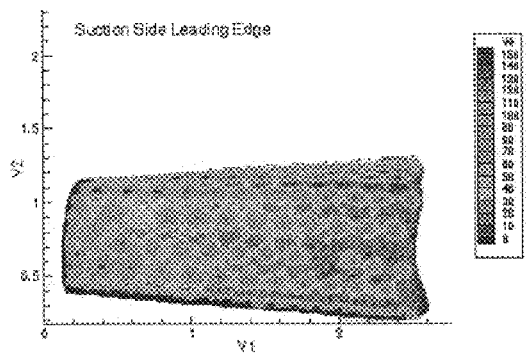
Figure 6D:
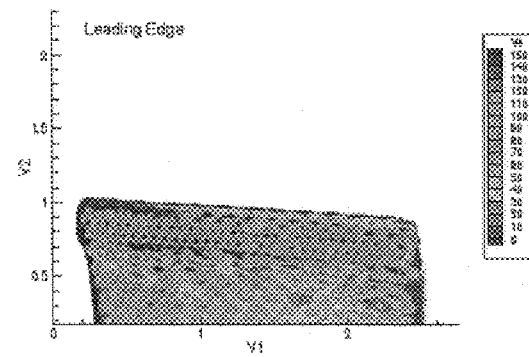

The nomenclature in equation (1) are normally defined as follows: $\rho$—airfoil material density; $C_p$—airfoil material specific heat; h—convective heat transfer coefficient; k—airfoil material thermal conductivity; $T_c$—temperature of air flowing through airfoil; $t_h$—airfoil surface wall thickness; $T_m$—airfoil surface temperature; $T_{m,x}$—temperature difference between adjacent pixels of the same frame; $T_{m,t}$—temperature difference of same pixel between subsequent frames; $\Delta t$—refers to time difference between subsequent frames; and, $\Delta x$—discrete pixel width. The energy balance considers convective heat transfer from the pixel to the cooling air flowing through the airfoil, energy storage within a pixel-sized mass $51_a$ (FIG. 5) of thickness $t_h$ and conduction to/from the four adjacent pixels $51_{b-e}$. In one form of the present invention the term "pseudo-heat transfer coefficient" is used because the actual thickness at each pixel is unknown and hence assumed to be evenly distributed. However, in an alternate form the actual thickness at each pixel is known and an assumption as to it's distribution is not needed.

In the first step in the data reduction procedure, equation (1) is solved numerically using a finite differencing method to yield the "pseudo heat transfer coefficient" at each pixel location. Please note that the subscripts i, j and n in equation (2) denote x, y and time indexing respectfully.

$$\rho C_p t_h(T_{m:i,j,n+1}-T_{m:i,j,n})/(T_{i,j,n+1}-t_{i,j,n})=h(t_{m:i,j,n}-T_{c:i})+$$
$$k(T_{m:i,j,n}-T_{m:i-1,j,n})t_h/\Delta x^2+(T_{m:i,j,n}-T_{m:i+1,j,n})t_h\Delta x^2+k$$
$$(T_{m:i,j,n}-T_{m:i-1,j,n})t_h/\Delta x^2+k(T_{m:i,j,n}-T_{m:i+1,j,n})t^h/\Delta x^2 \quad (2)$$

The heat transfer coefficient (h) values that are calculated for each pixel and time step and the respective heat transfer coefficients are then time averaged for each pixel. It is understood that the heat transfer coefficient values during the heat-up and cool down transients may not be exactly the same values due to flow conditions not being substantially identical during the heat-up and cool down phases of the test technique; nevertheless, the heat transfer coefficient values are comparable. If the flow conditions during heat-up and cool down are reasonably close, the heat transfer coefficient values should be very close. An example of typical heat transfer coefficient plots for an advanced gas turbine engine blade is shown in FIG. 6. Bench tests utilizing infrared thermal imaging techniques are generally conducted at temperatures within the range of about 200° F. to about 500° F. and airflow pressure ratios within a range of about 1.5 and about 7. In one embodiment the thermal imaging is done at 400° F. However, other pressure ratios and temperature are contemplated herein.

It is difficult or impossible to assess the engine worthiness of a gas turbine engine part based on heat transfer inspection at near ambient conditions without separating the convective and conduction components. This is because at near ambient test conditions the materials that gas turbine engine components of interest are made of have low convective coefficients and conduction dominates, while at gas turbine engine operating conditions the opposite is true. In one form the material of interest are superalloys. As used herein near ambient condition is intended to include typical temperatures used for bench testing, and generally are within the range of about 200° F. to about 500° F. However, other temperatures are contemplated herein. The techniques of the present invention provide results that separate the heat transfer associated with convection from conduction at near ambient conditions.

In one form of the present invention an individual blade design has been analyzed to determine a baseline or master set of heat transfer data. This baseline or master set of data will typically be generated during the design and development phases of an engine program. The baseline/master heat transfer data will be determined using analytical and empirical techniques that are generally known to one of ordinary skill in the art. The hardware condition after engine running will be compared to pre-run heat transfer coefficient data to establish nominal values, and/or maximum and/or minimum values on a pixel by pixel basis. Once generated, the master data would be stored on a computer and made available to those needing to verify component quality, such as but not limited to manufacturers and overhaul/repair facilities. The information could be transfered via standard digital communication techniques such as but not limited to modem, file transfer protocol, Zip disc, CD, and any other technique available to one of ordinary skill in the art to transfer data. It is understood that a copy of the master data could be stored at a central computer, regional computers, and/or stored at each location desiring access to the information.

The master set of data would be used to assess the worthiness of new, used, repaired, and/or modified parts. The master data and will be compared with heat transfer data obtained for a specific part by the methods and techniques described herein. The comparison of the data of the specific part and master data set is useable in, but not intended to be limited to, a manufacturing inspection environment, field replacement environment, machining and repair environment, design and development. Further, data developed for individual parts from the infrared thermal image testing techniques would be stored in a computer so that historical records could be maintained and referred to as needed.

Figure 7:
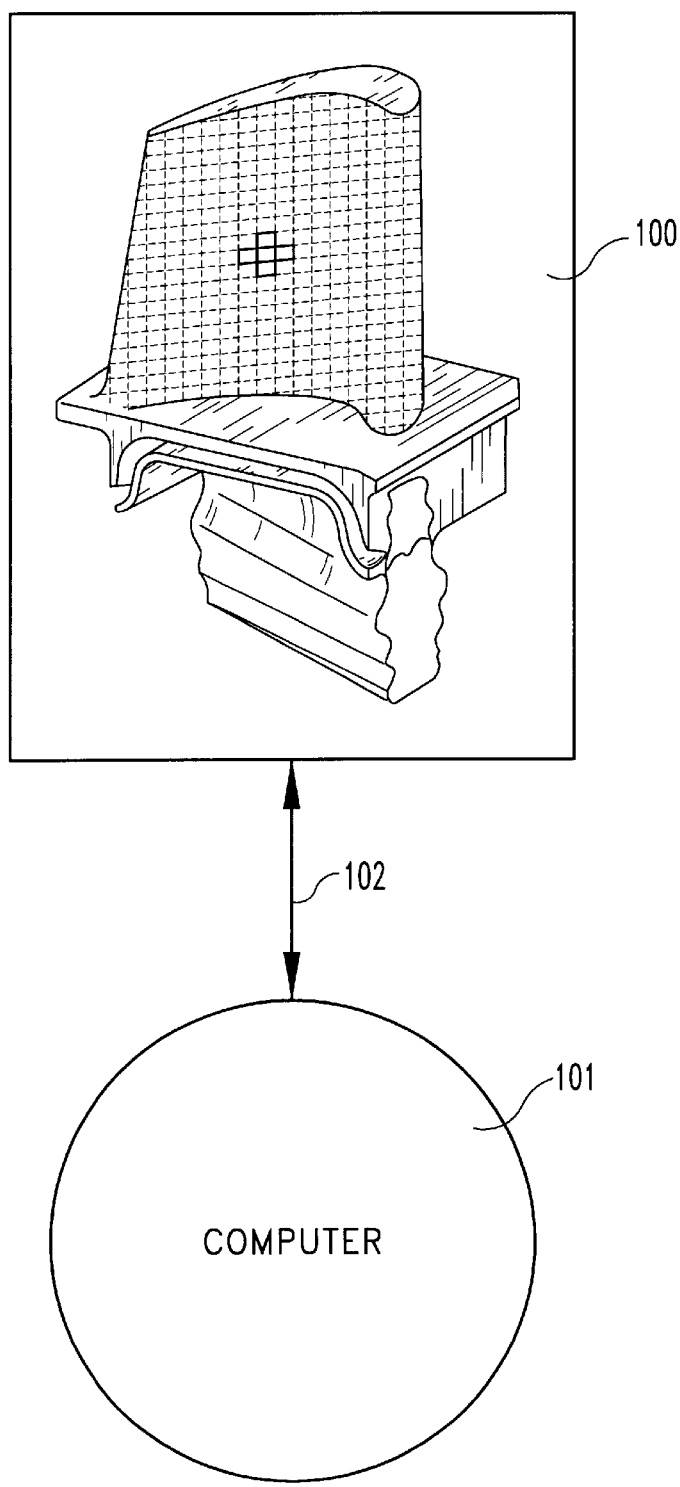
FIG. 7 is a illustrative view of another embodiment of a thermal imaging system of the present invention.

With reference to FIG. 7, there is illustrated a schematic of a thermal imaging system 100 connected with a computer 101 via a data transfer system 102. The thermal imaging system 100 is substantially identical to the system 50 previously described. The part heat transfer data acquired from the obtained from the part will be acquired and analyzed and then compared to the master data available from computer 101.

All publications, patents, and patent applications cited in this specification are herein incorporated by reference as if each individual publication, patent, or patent application were specifically and individually indicated to be incorporated by reference and set forth in its entirety herein. While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the invention are desired to be protected. The source code of various computer programs useful in performing operations according to the present invention are provided as follows:

```
      DIMENSION TEMP(349,404,40),regress(349,404)
      DIMENSION slope(349,404),incl(349,404),x(40),y(40)
      DIMENSION TIME(349,404,40)
      DIMENSION junk(6)
      integer fretart,trend
      CHARACTER fname*12
      INTEGER*2 junk
      INTEGER*2 MONTH,DAY,YEAR,HOUR,MIN,SEC,MID,HEI,MIDA,HEIA,
     &          IMID,IHEI
      INTEGER*2 FRA,NOL,T1,T2,T3,T5,MIDTEMP,SENSTVY,nlevels
      INTEGER*2 NUMBER(5639840)    ! 5639840 = 349 x 404 x 40   pcs
      INTEGER*4 T4
      CHARACTER TITLE*132
      CHARACTER*1 BIG(11279850),save1,save2        ! 5639840 x 2 + 170 pcs
      COMMON /input/title,month,day,year,hour,min,sec,wida,heia,
     &fra,nol,t1,t2,t3,t4,t5,midtemp,senstvy,nlevels,junk,number
      EQUIVALENCE (TITLE,BIG(1))
c     TSCALE=.05    DELAY=2000.
c
c     read in frame number for transient decay calculations
c
      OPEN(unit=5,file='Frame-in.dat')
      write(0,*)'Enter Binary File Name'
      read(*,'(a12)')fname
      write(0,*)'Enter Frame Start & End numbers'
      read(*,*)frstart,trend      !read frame start and end
      write(0,*)'Enter Coolant Temp in degC'
      read(*,*)tclnt
      write(0,*)'Enter Lowest Temp in degC'
      read(*,*)tlow
      write(0,*)'Enter Hottest Frame No.'
      read(*,*)nhotfr
      read(*,*)
      close(unit=5)

OPEN(Unit=10,file=fname,form='binary')
      OPEN(unit=6,file='sfout.dat')
      write(0,*)frstart,trend
      WRITE (0,*)' READING DATA'
      READ(10,end=10) (big(i),i=1,11279850)
      close(unit=10)

c**** Swapping bytes not required if run on an INTEL machine

WRITE (0,*)' SNAPPING BYTES'
      DO I=129,166,2
         save1= BIG(I)
         BIG(I)= BIG(I+1)                    ! INTERCHANGE BYTES FOR MONTH, DAY, .... T3
         BIG(I+1)= save1
      ENDDO
      save1= BIG(155)
      BIG(155)= BIG(157)
      BIG(157)= save1
      save1= BIG(156)
      BIG(156)= BIG(158)
      BIG(158)= save1                        ! INTERCHANGE T4 BYTES nbytes=heia*wida*2*fra+166

DO I=167,NBYTES,2
         save1= BIG(I)
         BIG(I)= BIG(I+1)                    ! INTERCHANGE BYTES FOR TEMPERATURES
         BIG(I+1)= save1
      ENDDO NIMAGE=(NBYTES-166)/2/HEIA/WIDA
      WRITE (0,*)' IMAGE WIDTH,HEIGHT,WIDA,HEIA,' # OF FRAMES ',NIMAGE WRITE(6,20)'(A8,1x,A12)')'FILENAME ',FNAME
      WRITE(6,20) TITLE
      WRITE(0,20) TITLE
20    FORMAT(1X,A132)
      WRITE(6,*)'MONTH  ',MONTH
      WRITE(6,*)'DAY    ',DAY
      WRITE(6,*)'YEAR   ',YEAR
      WRITE(6,*)'HOUR   ',HOUR
      WRITE(6,*)'MIN    ',MIN
      WRITE(6,*)'SEC    ',SEC
      WRITE(6,*)'WIDTH OF FRAME  ',WIDA
      WRITE(6,*)'HEIGHT OF FRAME ',HEIA
      WRITE(6,*)'NO. OF FRAMES   ',FRA
      WRITE(6,*)'NO. LINES       ',NOL
      WRITE(6,*)'ELAPSED TIME (TRIGGER TO 1ST PIXEL) - MICROSEC ',T1
      WRITE(6,*)'DELTA PIXEL TIME - NANOSEC    ',T2
      WRITE(6,*)'DELTA LINE TIME - MICROSEC    ',T3
      WRITE(6,*)'DELTA FRAME TIME - MICROSEC   ',T4
      WRITE(6,*)' IMAGE WIDTH,HEIGHT',WIDA,HEIA,' # OF FRAMES ',NIMAGE
      T1S=T1*1.E-6-0.00403          ! TIME TO FIRST PIXEL    ! JFR 11/22/94
      T2S=T2*1.E-9                  ! DELTA PIXEL TIME
      T3S=T3*1.E-6                  ! DELTA LINE TIME
      T4S=T4*1.E-6                  ! DELTA FRAME TIME
      IF(DELAY.GT.T4S) T4S=DELAY
      WRITE(0,*)' CONVERTING NUMBERS TO TEMPERATURES AND CALCULATING TI
     &ME'
      WRITE (6,*)'T5,MIDTEMP,SENSTY, NLVLS,',t5,midtemp,sensty,nlevels
      WRITE (0,*)junk(1),junk(2),junk(3),junk(4)
      WRITE (0,*)number(1),number(2),number(3),number(4)
      WRITE (0,*)number(5),number(6),number(7),number(8)
      WRITE (0,*)number(109),number(110),number(111),number(112)
      WRITE (0,*)' CONVERTING NUMBERS TO TEMPERATURES'
      DO IMAGE=1,NIMAGE
         DO I=1,HEIA
            DO J=1,WIDA
                                       TSCALE
               TEMP(J,I,IMAGE)=NUMBER((IMAGE-1)*WIDA*HEIA+(I-1)*WIDA+J)
               TIME(J,I,IMAGE)=T1S+(J-1)*T2S+(I-1)*T3S+(IMAGE-1)*T4S
            enddo
         enddo
c
c        exclude pixels with temperatures less than tlow C
         do i=1,heia
            do j=1,wida
               incl(j,i)=1
               do image=1,nimage
                  imagen=hotfr
                  if(temp(j,i,image).lt.tlow)incl(j,i)=0
               enddo
            enddo
         enddo
c
c        average pixels around each to location
c
         regressmin=1.0
         regressmax=0.0
         regressavg=0.0
         numregress=0
         do i=1,wida
            do j=1,heia
```

```
slope(i,j)=0.0
regress(i,j)=0.0
if(incl(i,j).eq.1)then
    do image=fcstart,frend
        y(image)=alog(tcint-temp(i,j,image))
        x(image)=time(i,j,image)
    enddo
    num=0
    sumxy=0.0
    sumx=0.0
    sumy=0.0
    sumx2=0.0
    sumy2=0.0
    do image=fcstart,frend
        num=num+1
        sumxy=sumxy+x(image)*y(image)
        sumx=sumx+x(image)
        sumy=sumy+y(image)
        sumx2=sumx2+x(image)*x(image)
        sumy2=sumy2+y(image)*y(image)
    enddo
    slopeact=(num*sumxy-sumx*sumy)/(num*sumx2-sumx*sumx)
    yint=sumy/num-slopeact*sumx/num
    sumy2=0
    do image=fcstart,frend
        sumy2=sumy2 + (y(image)-(yint+slopeact*x(image)))**2
    enddo
    regress(i,j)=(1.-sumy2/(num*sumy*sumy))
    if(regress(i,j).lt.regressmin)regressmin=regress(i,j)
    if(regress(i,j).gt.regressmax)regressmax=regress(i,j)
    regressavg=regressavg+regress(i,j)
    numregress=numregress+1
    slope(i,j)=-slopeact
endif
enddo
enddo
regressavg=regressavg/numregress
write(0,*)'REGRESS MIN',regressmin
write(0,*)'REGRESS MAX',regressmax
write(0,*)'REGRESS avg',regressavg
write(6,*)'REGRESS MIN',regressmin
write(6,*)'REGRESS MAX',regressmax
write(6,*)'REGRESS avg',regressavg
write(6,*)'TCINT degC=',tcint
write(6,*)'TLOW degC=',tlow
close(6)
OPEN(unit=6,file='slope.dat')
write(6,']' X(IN.) Y(IN.) slope(h-int/m*cp)1 Regress'
do i=1,wida
    xpix=i*0.01
    do j=1,heia
        ypix=(heia-j+1)*0.01
        write(6,'(2F9.4,3x,g12.6,2x,f6.4)')
1       xpix,ypix,slope(i,j),regress(i,j)
    enddo
enddo
close(unit=6)
stop
end
```

```
      DIMENSION TEMP(349,404,50),regress(349,404)
      DIMENSION slope(349,404),incl(349,404),x(50),y(50)
      DIMENSION TIME(349,404,50)
      DIMENSION junk(6)
      Integer trstart,trend
      CHARACTER fname*12
      INTEGER*2 junk
      INTEGER*2 MONTH,DAY,YEAR,HOUR,MIN,SEC,MID,HEI,MIDA,HEIA,
     &          IMID,IHEI
      INTEGER*2 FRA,NOL,T1,T2,T3,T5,MIDTEMP,SENSTVY,nlevels
      INTEGER*2 NUMBER( 7049800 )     ! 14099770 x 2 + 170   pcs
      COMMON /input/title,month,day,year,hour,min,sec,wida,heia,
     &fra,nol,t1,t2,t3,t4,t5,midtemp,senstvy,nlevels,junk,number
      INTEGER*4 T4                    ! 7049800 = 349 x 404 x 50    pcs
      CHARACTER TITLE*132
      'VALENCE (TITLE,BIG(1))
      LE=0;   TSCALE=.05
      GV=1000. DELAY=2000.
c
c     read in (frame number for transient decay calculations
c
      OPEN(unit=5,file='Frame-in.dat')
      write(0,*)'Enter Binary File Name'
      read(*,'(a12)')fname
      write(0,*)'Enter Frame Start & End numbers'
      read(*,*)frstart,trend   !read frame start and end
      write(0,*)'Enter Coolant Temp in degC'
      read(*,*)tclnt
      write(0,*)'Enter Lowest Temp in degC'
      read(*,*)tclow
      write(0,*)'Enter Highest Temp Frame No:'
      read(*,*)nhotfr
      close(unit=5)
c
      OPEN(Unit=10,file=fname,form='binary')
      OPEN(unit=6,file='afout.dat')
      WRITE (0,*)'restart,trend
      write(0,*)tclnt
c     WRITE (0,*) ' READING DATA'
      READ(10,end=10) (big(i),i=1,14099770)
      close(unit=10)
6V c**** Swapping bytes not required if run on an INTEL machine
      WRITE (0,*),' SWAPPING BYTES'
      DO I=129,166,2
         save1= BIG(I)
         BIG(I)= BIG(I+1)
         BIG(I+1)= save1
      ENDDO
      save1= BIG(155)
      BIG(155)= BIG(157)
      BIG(157)= save1
      save1= BIG(156)
      BIG(156)= BIG(158)
      BIG(158)= save1
c
      nbytes=heia*wida*2*fra+166
c
      DO I=167,NBYTES,2
         save1= BIG(I)
         BIG(I)= BIG(I+1)
         BIG(I+1)= save1
```

```
      ENDDO
c
c     INTERCHANGE BYTES FOR TEMPERATURES

NIMAGE=(NBYTES-166)/2/HEIA/WIDA
      WRITE (0,*) ' IMAGE WIDTH,HEIGHT,WIDA,HEIA,   # OF FRAMES ',NIMAGE

WRITE(6,*)'(A4,1x,A12)')'FILENAME ',FNAME
      WRITE(6,20) TITLE
      WRITE(0,20) TITLE
20    FORMAT(1X,A132)
      WRITE(6,*)'MONTH    ',MONTH
      WRITE(6,*)'DAY      ',DAY
      WRITE(6,*)'YEAR     ',YEAR
      WRITE(6,*)'HOUR     ',HOUR
      WRITE(6,*)'MIN      ',MIN
      WRITE(6,*)'SEC      ',SEC
      WRITE(6,*)'WIDTH OF FRAME     ',WIDA
      WRITE(6,*)'HEIGHT OF FRAME    ',HEIA
      WRITE(6,*)'NO. OF FRAMES      ',FRA
      WRITE(6,*)'NO. LINES          ',NOL
      WRITE(6,*)'ELAPSED TIME (TRIGGER TO 1ST PIXEL) - MICROSEC ',T1
      WRITE(6,*)'DELTA PIXEL TIME - NANOSEC                     ',T2
      WRITE(6,*)'DELTA LINE TIME - MICROSEC                     ',T3
      WRITE(6,*)'DELTA FRAME TIME - MICROSEC                    ',T4
      WRITE(6,*)' IMAGE WIDTH,HEIGHT,WIDA,HEIA,   # OF FRAMES ',NIMAGE
      T1S=T1*1.E-6+0.00403      ! TIME TO FIRST PIXEL    JFR 11/22/94
      T2S=T2*1.E-9              ! DELTA PIXEL TIME
      T3S=T3*1.E-6              ! DELTA LINE TIME
      T4S=T4*1.E-6              ! DELTA FRAME TIME
      IF(DELAY.GT.T4S) T4S=DELAY
      WRITE (0,*) ' CONVERTING NUMBERS TO TEMPERATURES AND CALCULATING TI
     1ME'
      WRITE(6,*)'T5,MIDTEMP,SENSTY,NLVLS',t5,midtemp,senstvy,nlevels
      WRITE(0,*)junk(1),junk(2),junk(3),junk(4)
      WRITE(0,*)number(1),number(2),number(3),number(4)
      WRITE(0,*)number(5),number(6),number(7),number(8)
      WRITE(0,*)number(109),number(110),number(111),number(112)
      WRITE(0,*) ' CONVERTING NUMBERS TO TEMPERATURES'
      DO IMAGE=1,NIMAGE
         DO J=1,HEIA
            DO I=1,WIDA
              TEMP(J,I,IMAGE)=NUMBER((IMAGE-1)*WIDA*HEIA+(I-1)*WIDA+J)
                                                  TSCALE
              TIME(J,I,IMAGE)=T1S+(J-1)*T2S+(I-1)*T3S+(IMAGE-1)*T4S
            enddo
         enddo
      enddo
c
c     exclude pixels with temperatures less than tlow  c
c
      do i=1,heia
         incl(j,i)=1
         do image=1,nimage
            image=nhotfr   if(temp(j,i,image).lt.tlow)incl(j,i)=0
         enddo
      enddo
c
c     average pixels around each tc location
c
      regressmin=1.0
      regressmax=0.0
      regressavg=0.0
      numregress=0
      do i=1,wida
```

```
      do j=1,hela
        slope(i,j)=0.0
        regress(i,j)=0.0
        if(incl(i,j).eq.1)then
          do image=fretart,frend
            y(image)=alog(temp(i,j,image)-tcint)
            x(image)=time(i,j,image)
          enddo
          num=0
          sumxy=0.0
          sumx=0.0
          sumy=0.0
          sumx2=0.0
          sumy2=0.0
          do image=fretart,frend
            num=num+1
            sumxy=sumxy+y(image)*x(image)
            sumx=sumx+x(image)
            sumy=sumy+y(image)
            sumx2=sumx2+x(image)*x(image)
            sumy2=sumy2+y(image)*y(image)
          enddo
          slopeact=(num*sumxy-sumx*sumy)/((num*sumx2-sumx*sumx))
          yint=sumy/num-slopeact*sumx/num
          sumy2=0
          do image=fretart,frend
            sumy2=sumy2 + (y(image)-(yint+slopeact*x(image
          enddo
          regress(i,j)=sqrt(1.-sumy2/((num*sumy2-sumy*sumy))
          if(regress(i,j).lt.regressmin)regressmin=regress(i,j)
          if(regress(i,j).gt.regressmax)regressmax=regress(i,j)
          regressavg=regressavg+regress(i,j)
          numregress=numregress+1
          slope(i,j)=-slopeact
        endif
      enddo
    enddo
    regressavg=regressavg/numregress write(0,*)'REGRESS MIN',regressmin
    write(0,*)'REGRESS MAX',regressmax
    write(0,*)'REGRESS avg',regressavg
    write(6,*)'REGRESS MIN',regressmin
    write(6,*)'REGRESS MAX',regressmax
    write(6,*)'REGRESS avg',regressavg
    write(6,*)'TCINT degC=',tcint
    write(6,*)'TLOW degC=',tlow
    close(6)
    OPEN(unit=6,file='slope.dat')
    write(6,*)' X(IN.) Y(IN.) Slope(h-int/m*cp)1 Regress'
    do i=1,wida
      xpix=i*0.01
      do j=1,hela
        ypix=(hela-j+1)*0.01
        write(6,'(2F9.4,3x,g12.6,2x,f6.4)')
1        xpix,ypix,slope(i,j),regress(i,j)
      enddo
    enddo
    close(unit=6)
c
    stop
    end
```

```
      DIMENSION TEMP(260,200,50),reghot(260,200),regcld(260,200)
      DIMENSION alphot(260,200),incl(260,200),x(50),y(50)
      DIMENSION TIME(260,200,50),alpcld(260,200)
      DIMENSION junk(6)
      integer tsthot,frendhot,tretcold,trendold
      CHARACTER fname*12
      INTEGER*2 junk
      INTEGER*2 MONTH,DAY,YEAR,HOUR,MIN,SEC,MID,HEI,MID,HEIA,
     &          IWID,IHEI
      INTEGER*2 FRA,NOL,T1,T2,T3,T5,MIDTEMP,SENSTVY,nlevels
      INTEGER*2 NUMBER (2600000)       !  2600000 = 260 x 200 x 50    pcs
      INTEGER*4 T4
      CHARACTER TITLE*128                                              pcs
      CHARACTER*1 BIG(5200170),savel,savea   ! 2600000 x 2 + 170
      COMMON /input/title,month,day,year,hour,min,sec,wida,heia,
     &fra,nol,t1,t2,t3,t4,t5,midtemp,senstvy,nlevels,junk,number
      EQUIVALENCE (TITLE,BIG(1))
      TSCALE=.05
      DELAY=2000.

c
c     read in frame number for transient decay calculations
c
      OPEN(unit=5,file='Frame-in.dat')
      read(5,'(a12)')fname
      read(5,*)tsthot,frendhot,tretcold,trendold
      read(5,*)thot,tcint
      read(5,*)tlow
      read(5,*)nhotfr
      close(unit=5)

OPEN(Unit=10,file=fname,form='unformatted')
      OPEN(unit=6,file='afout.dat')
      WRITE (0,*)frethot,frendhot,fretcold,frendold
      write(0,*)thot,tcint
      WRITE (0,*)      ! READING DATA
      READ(10,end=10) (big(i),i=1,5200170)
 10   close(unit=10)
c
c **** Swapping bytes not required if run on an INTEL machine
c
      WRITE (0,*) ' SWAPPING BYTES'
      DO I=129,166,2                   ! INTERCHANGE BYTES FOR MONTH, DAY, ..... T3
         savel= BIG(I)
         BIG(I)= BIG(I+1)
         BIG(I+1)= savel
      ENDDO
         savel= BIG(155)
         BIG(155)= BIG(157)
         BIG(157)= savel
         savel= BIG(156)
         BIG(156)= BIG(158)
         BIG(158)= savel
c
      nbytes=heia*wida*2*fra+166
c
      DO I=167,NBYTES,2                ! INTERCHANGE BYTES FOR TEMPERATURES
         savel= BIG(I)
         BIG(I)= BIG(I+1)
         BIG(I+1)= savel
      ENDDO
c
      NIMAGE=(NBYTES-166)/2/HEIA/WIDA
      WRITE (0,*) ' IMAGE WIDTH,HEIGHT ',WIDA,HEIA,' # OF FRAMES ',NIMAGE
c
      WRITE(6,'(A8,1X,A12)')'FILENAME ',FNAME
```

```
      WRITE(6,20) TITLE
      WRITE(0,20) TITLE
 20   FORMAT(1X,A122)
      WRITE(6,*)'MONTH ',MONTH
      WRITE(6,*)'DAY   ',DAY
      WRITE(6,*)'YEAR  ',YEAR
      WRITE(6,*)'HOUR  ',HOUR
      WRITE(6,*)'MIN   ',MIN
      WRITE(6,*)'SEC   ',SEC
      WRITE(6,*)'WIDTH OF FRAME  ',WIDA
      WRITE(6,*)'HEIGHT OF FRAME ',HEIA
      WRITE(6,*)'NO. OF FRAMES   ',FRA
      WRITE(6,*)'NO. LINES       ',NOL
      WRITE(6,*)'ELAPSED TIME (TRIGGER TO 1ST PIXEL) - MICROSEC ',T1
      WRITE(6,*)'DELTA PIXEL TIME - NANOSEC  ',T2
      WRITE(6,*)'DELTA LINE TIME  - MICROSEC ',T3
      WRITE(6,*)'DELTA FRAME TIME - MICROSEC ',T4
      WRITE(6,*)' IMAGE WIDTH,HEIGHT ',WIDA,HEIA,' # OF FRAMES ',NIMAGE
     &                                                  ( JFR 11/22/94
      T1S=T1*1.E-6+0.00403    ! TIME TO FIRST PIXEL
      T2S=T2*1.E-9            ! DELTA PIXEL TIME
      T3S=T3*1.E-6            ! DELTA LINE TIME
      T4S=T4*1.E-6  T4S=DELAY ! DELTA FRAME TIME
      IF(DELAY.GT.T4S) T4S=DELAY
      WRITE(0,*)  ! CONVERTING NUMBERS TO TEMPERATURES AND CALCULATING TI
     &ME'
      WRITE (6,*) T5,MIDTEMP,SENSTY, NLVLS',t5,midtemp,senstvy,nlevels
      DO IMAGE=1,NIMAGE
         DO I=1,HEIA
            DO J=1,WIDA
              TEMP(J,I,IMAGE)=NUMBER((IMAGE-1)*WIDA*HEIA+(I-1)*WIDA+J) *
     &                         TSCALE
              TIME(J,I,IMAGE)=T1S+(J-1)*T2S+(I-1)*T3S+(IMAGE-1)*T4S
            enddo
         enddo
      enddo
c
c     exclude pixels with temperatures less than tlow c
c
      do i=1,heia
         do j=1,wida
            incl(j,i)=1
            imagenhotfr
            if(temp(j,i,image).lt.tlow)incl(j,i)=0
         enddo
      enddo
c
c     calculate thermal response hot rise
c
      reghotmin=1.0
      reghotmax=0.0
      reghotavg=0.0
      numreghot=0
      do i=1,wida
         do j=1,heia
            alphot(i,j)=0.0
            reghot(i,j)=0.0
            if(incl(i,j).eq.1)then
               do image=fretohot,frendhot
                  y(image)=alog(tcint-temp(i,j,image))
                  x(image)=time(i,j,image)
               enddo
               num=0
               sumx=0.0
               sumy=0.0
```

```
sumx2=0.0
sumy2=0.0
do image=frsthot,frendhot
    num=num+1
    sumxy=sumxy+y(image)*x(image)
    sumx=sumx+x(image)
    sumy=sumy+y(image)
    sumx2=sumx2+x(image)*x(image)
    sumy2=sumy2+y(image)*y(image)
enddo
slopeact=(num*sumxy-sumx*sumy)/(num*sumx2-sumx*sumx)
yint=sumy/num-slopeact*sumx/num
sumy2=0
do image=frsthot,frendhot
    sumy2=sumy2 + (y(image)-(yint+slopeact*x(image)))**2
enddo
reghot(i,j)=(1.-sumy2/(num*sumy2-sumy*sumy))
if(reghot(i,j).lt.reghotmin)reghotmin=reghot(i,j)
if(reghot(i,j).gt.reghotmax)reghotmax=reghot(i,j)
reghotavg=reghotavg+reghot(i,j)
numreghot=numreghot+1
alphot(i,j)=-slopeact
endif
    enddo
enddo
reghotavg=reghotavg/numreghot write(0,*)'REGRESS HOT MIN',reghotmin
write(0,*)'REGRESS HOT MAX',reghotmax
write(0,*)'REGRESS HOT AVG',reghotavg
write(6,*)'REGRESS HOT MIN',reghotmin
write(6,*)'REGRESS HOT MAX',reghotmax
write(6,*)'REGRESS HOT AVG',reghotavg
write(6,*)'TCLNT HOT degC=',thot
write(6,*)'TLOW degC=',tlow
OPEN(unit=7,file='alphot.dat')
write(7,*)' X(IN.) Y(IN.) Slope(h-int/m*cp)i  Regress'
do i=1,wida
    xpix=i*0.01
    do j=1,hela
        ypix=(hela-j+1)*0.01
        write(7,'(2F9.4,3X,g12.6,2X,f6.4)')
    1       xpix,ypix,alphot(i,j),reghot(i,j)
    enddo
enddo
close(unit=7)

c
c calculate thermal response of cold decay
c
regcldmin=1.0
regcldmax=0.0
regcldavg=0.0
numregcld=0
do i=1,wida
    do j=1,hela
        alpcld(i,j)=0.0
        regcld(i,j)=0.0
        if(incl(i,j).eq.1)then
            do image=frstcld,frendcld
                y(image)=alog(tcint-temp(i,j,image))
                x(image)=time(i,j,image)
            enddo
            num=0
            sumxy=0.0
```

```
sumx=0.0
sumy=0.0
sumx2=0.0
sumy2=0.0
do image=frstcld,frendcld
    num=num+1
    sumxy=sumxy+y(image)*x(image)
    sumx=sumx+x(image)
    sumy=sumy+y(image)
    sumx2=sumx2+x(image)*x(image)
    sumy2=sumy2+y(image)*y(image)
enddo
slopeact=(num*sumxy-sumx*sumy)/(num*sumx2-sumx*sumx)
yint=sumy/num-slopeact*sumx/num
sumy2=0
do image=frstcld,frendcld
    sumy2=sumy2 + (y(image)-(yint+slopeact*x(image)))**2
enddo
regcld(i,j)=sqrt(1.-sumy2/(num*sumy2-sumy*sumy))
if(regcld(i,j).lt.regcldmin)regcldmin=regcld(i,j)
if(regcld(i,j).gt.regcldmax)regcldmax=regcld(i,j)
regcldavg=regcldavg+regcld(i,j)
numregcld=numregcld+1
alpcld(i,j)=-slopeact
endif
    enddo
enddo
regcldavg=regcldavg/numregcld write(0,*)'REGRESS COLD MIN',regcldmin
write(0,*)'REGRESS COLD MAX',regcldmax
write(0,*)'REGRESS COLD AVG',regcldavg
write(6,*)'REGRESS COLD MIN',regcldmin
write(6,*)'REGRESS COLD MAX',regcldmax
write(6,*)'REGRESS COLD AVG',regcldavg
write(6,*)'TCLNT degC=',tcint
write(6,*)'TLOW degC=',tlow
close(6)
OPEN(unit=7,file='alpcld.dat')
write(7,*)' X(IN.) Y(IN.) Slope(h-int/m*cp)i  Regress'
do i=1,wida
    xpix=i*0.01
    do j=1,hela
        ypix=(hela-j+1)*0.01
        write(6,'(2F9.4,3X,g12.6,2X,f6.4)')
    1       xpix,ypix,alpcld(i,j),regcld(i,j)
    enddo
enddo
close(unit=7)

stop
end
```

```
      DIMENSION TEMP(260,200,50),reghot(260,200),regcld(260,200)
      DIMENSION siphot(260,200),incl(260,200),slpcld(260,200),x(50),y(50)
      DIMENSION TIME(260,200,50),slpcld(260,200)
      DIMENSION junk(6)
      integer fratcold,fratcold,frendcld
      CHARACTER fname*12
      INTEGER*2 junk
      INTEGER*2 MONTH,DAY,YEAR,HOUR,MIN,SEC,MID,HEI,WIDA,HEIA,
     1             IMID,IHEI
      INTEGER*2 FRA,NOL,T1,T2,T3,T5,MIDTEMP,SENSTVY,nlevels
      INTEGER*2 NUMBER( 2600000)  ! 2600000 = 260 x 200 x 50    pcs
      INTEGER*4 T4
      CHARACTER TITLE*128
      CHARACTER*1 BIG(5200170),save1,savea    ! 2600000 x 2 + 170   pcs
      COMMON /input/title,month,day,year,hour,min,sec,wida,hela,
     &fra,nol,t1,t2,t3,t4,t5,midtemp,senstvy,nlevels,junk,number
      EQUIVALENCE (TITLE,BIG(1))
      TSCALE=.05
c----     DELAY = 2000.
c     read in frame number for transient decay calculations
c
      OPEN(unit=5,file='frame-in.dat')
      read(5,'(a12)')fname
      read(5,*)frathot,frendhot,fratcld,frendcld
      read(5,*)thot,tcint
      read(5,*)tlow
        read(5,*)inhottr
      close(unit=5)
c
      OPEN(unit=10,file=fname,form='unformatted')
      OPEN(unit=6,file='afout.dat')
      WRITE (0,*)frathot, frendhot,fratcld,frendcld
      write(0,*)thot,tcint
      WRITE (0,*) ' READING DATA'
      READ(10,end=10) (big(i),i=1,5200170)
      close(unit=10)
c
c **** Swapping bytes not required if run on an INTEL machine
      WRITE (0,*) ' SWAPPING BYTES'
      DO I=129,166,2                  ! INTERCHANGE BYTES FOR MONTH, DAY, ..., T3
      save1= BIG(I)
      BIG(I)= BIG(I+1)
      BIG(I+1)= save1
      ENDDO
      save1= BIG(155)
      BIG(155)= BIG(157)
      BIG(157)= save1
      save1= BIG(156)
      BIG(156)= BIG(158)
      BIG(158)= save1
c
      nbytes=hela*wida*2*fra+166
c
      DO I=167,NBYTES,2                ! INTERCHANGE BYTES FOR TEMPERATURES
      save1= BIG(I)
      BIG(I)= BIG(I+1)
      BIG(I+1)= save1
      ENDDO
c
      NIMAGE=(NBYTES-166)/2/HEIA/WIDA
      WRITE (0,*) ' IMAGE WIDTH,HEIGHT',WIDA,HEIA,' # OF FRAMES ',NIMAGE
c
      WRITE(6,'(A8,1x,A12)')'FILENAME ',FNAME
```

```
      WRITE(6,20) TITLE
      WRITE(0,20) TITLE
 20   FORMAT(1X,A128)
      WRITE(6,*) 'MONTH ',MONTH
      WRITE(6,*) 'DAY   ',DAY
      WRITE(6,*) 'YEAR  ',YEAR
      WRITE(6,*) 'HOUR  ',HOUR
      WRITE(6,*) 'MIN   ',MIN
      WRITE(6,*) 'SEC   ',SEC
      WRITE(6,*) 'WIDTH OF FRAME   ',WIDA
      WRITE(6,*) 'HEIGHT OF FRAME  ',HEIA
      WRITE(6,*) 'NO. OF FRAMES    ',FRA
      WRITE(6,*) 'NO. LINES        ',NOL
      WRITE(6,*) 'ELAPSED TIME (TRIGGER TO 1ST PIXEL) - MICROSEC ',T1
      WRITE(6,*) 'DELTA PIXEL TIME - NANOSEC                     ',T2
      WRITE(6,*) 'DELTA LINE TIME - MICROSEC                     ',T3
      WRITE(6,*) 'DELTA FRAME TIME - MICROSEC                    ',T4
      WRITE(6,*) ' IMAGE WIDTH,HEIGHT',WIDA,HEIA,' # OF FRAMES ',NIMAGE
      T1S=T1*1.E-6+0.00403    ! TIME TO FIRST PIXEL     ! JFR 11/22/94
      T2S=T2*1.E-9            ! DELTA PIXEL TIME
      T3S=T3*1.E-6            ! DELTA LINE TIME
      T4S=T4*1.E-6            ! DELTA FRAME TIME
      IF(DELAY.GT.T4S) T4S=DELAY
      WRITE(0,*) ' CONVERTING NUMBERS TO TEMPERATURES AND CALCULATING TI
     1ME'
      WRITE (0,*) 'T5,MIDTEMP,SENSTY, NUVLS',T5,midtemp,senstvy,nlevels
      DO IMAGE=1,NIMAGE
      DO I=1,HEIA
      DO J=1,WIDA
       TEMP(J,I,IMAGE)=NUMBER((IMAGE-1)*WIDA*HEIA+(I-1)*WIDA+J) *
     1                 TSCALE
       TIME(J,I,IMAGE)=T1S+(J-1)*T2S+(I-1)*T3S+(IMAGE-1)*T4S
      enddo
      enddo
      enddo
c
c exclude pixels with temperatures less than tlow C
c
      do i=1,hela
      do j=1,wida
      incl(j,i)=1
        if(temp(j,i,image).lt.tlow)incl(j,i)=0
      enddo
      enddo
c
c calculate thermal response hot rise
c
      reghotmin=1.0
      reghotmax=0.0
      reghotavg=0.0
      numreghot=0
      do i=1,wida
      do j=1,hela
        slphot(i,j)=0.0
        reghot(i,j)=0.0
      if(incl(i,j).eq.1)then
      do image=frathot,frendhot
        y(image)=alog(thot-temp(i,j,image))
        x(image)=time(i,j,image)
      enddo
      num=0
      sumxy=0.0
      sumx=0.0
      sumy=0.0
```

```
            sumx2=0.0
            sumy2=0.0
            do image=frsthot,trendhot
              num=num+1
              sumxy=sumxy+y(image)*x(image)
              sumx=sumx+x(image)
              sumy=sumy+y(image)
              sumx2=sumx2+x(image)*x(image)
              sumy2=sumy2+y(image)*y(image)
            enddo
            slopeact=(num*sumxy-sumx*sumy)/(num*sumx2-sumx*sumx)
            yint=sumy/num-slopeact*sumx/num
            sumy2=0
            do image=frsthot,trendhot
              sumy2=sumy2 + (y(image)-(yint+slopeact*x(image)))**2
            enddo
            reghot(i,j)=(1.-sumy2/(num*sumy2-sumy*sumy))
            if(reghot(i,j).lt.reghotmin) reghotmin=reghot(i,j)
            if(reghot(i,j).gt.reghotmax) reghotmax=reghot(i,j)
            reghotavg=reghotavg+reghot(i,j)
            numreghot=numreghot+1
            slphot(i,j)=slopeact
          endif
        enddo
      enddo
      reghotavg=reghotavg/numreghot write(0,*)'REGRESS HOT MIN',reghotmin
      write(0,*)'REGRESS HOT MAX',reghotmax
      write(0,*)'REGRESS HOT AVG',reghotavg
      write(6,*)'REGRESS HOT MIN',reghotmin
      write(6,*)'REGRESS HOT MAX',reghotmax
      write(6,*)'REGRESS HOT AVG',reghotavg
      write(6,*)'TCLNT HOT degC=',tcint
      write(6,*)'TLOW degC=',tlow
      OPEN(unit=7,file='slphot.dat')
      write(7,*)' X(IN.) Y(IN.) Slope(h-int/m*cp)1 Regress'
      do i=1,wida
        xplx=i*0.01
        do j=1,hela
          yplx=(hela-j+1)*0.01
          write(7,'(2F9.4,3x,g12.6,2x,f6.4)')
     1         xplx,yplx,slphot(i,j),reghot(i,j)
        enddo
      enddo
      close(unit=7)

c
c calculate thermal response of cold decay
c
      regcldmin=1.0
      regcldmax=0.0
      regcldavg=0.0
      numregcld=0
      do i=1,wida
        do j=1,hela
          slpcld(i,j)=0.0
          regcld(i,j)=0.0
          if(inc(i,j).eq.1) then
            do image=frstcld,trendcld
              y(image)=alog(temp(i,j,image)-tcint)
              x(image)=etime(i,j,image)
            enddo
            num=0
            sumxy=0.0
            sumx=0.0
            sumy=0.0
            sumx2=0.0
            sumy2=0.0
            do image=frstcld,trendcld
              num=num+1
              sumxy=sumxy+y(image)*x(image)
              sumx=sumx+x(image)
              sumy=sumy+y(image)
              sumx2=sumx2+x(image)*x(image)
              sumy2=sumy2+y(image)*y(image)
            enddo
            slopeact=(num*sumxy-sumx*sumy)/(num*sumx2-sumx*sumx)
            yint=sumy/num-slopeact*sumx/num
            sumy2=0
            do image=frstcld,trendcld
              sumy2=sumy2 + (y(image)-(yint+slopeact*x(image)))**2
            enddo
            regcld(i,j)=sqrt(1.-sumy2/(num*sumy2-sumy*sumy))
            if(regcld(i,j).lt.regcldmin) regcldmin=regcld(i,j)
            if(regcld(i,j).gt.regcldmax) regcldmax=regcld(i,j)
            regcldavg=regcldavg+regcld(i,j)
            numregcld=numregcld+1
            slpcld(i,j)=-slopeact
          endif
        enddo
      enddo
      regcldavg=regcldavg/numregcld write(0,*)'REGRESS COLD MIN',regcldmin
      write(0,*)'REGRESS COLD MAX',regcldmax
      write(0,*)'REGRESS COLD AVG',regcldavg
      write(6,*)'REGRESS COLD MIN',regcldmin
      write(6,*)'REGRESS COLD MAX',regcldmax
      write(6,*)'REGRESS COLD AVG',regcldavg
      write(6,*)'TCLNT degC=',tcint
      write(6,*)'TLOW degC=',tlow
      close(6)
      OPEN(unit=7,file='slpcld.dat')
      write(7,*)' X(IN.) Y(IN.) Slope(h-int/m*cp)1 Regress'
      do i=1,wida
        xplx=i*0.01
        do j=1,hela
          yplx=(hela-j+1)*0.01
          write(7,'(2F9.4,3x,g12.6,2x,f6.4)')
     1         xplx,yplx,slpcld(i,j),regcld(i,j)
        enddo
      enddo
      close(unit=7)

stop
      end
```

```
      DIMENSION TEMP(260,200,50),reghot(260,200),regcld(260,200)
      DIMENSION alphot(260,200),incl(260,200),x(50),y(50)
      DIMENSION TIME(260,200,50),mipcld(260,200)
      DIMENSION junk(6)
      integer frsthot,trendhot,trstcld,trendcld
      CHARACTER fname*12
      INTEGER*2 junk
      INTEGER*2 MONTH,DAY,YEAR,HOUR,MIN,SEC,MID,HEI,MIDA,HEIA,
     &               IMID,IHEI
      INTEGER*2 FRA,NOL,T1,T2,T3,T5,MIDTEMP,SENSTVY,nlevels
      INTEGER*2 NUMBER( 2600000)     ! 2600000 = 260 x 200 x 50     pcs
      INTEGER*4 T4
      CHARACTER TITLE*128
      CHARACTER*1 BIG(52001700),save1,save4     ! 2600000 x 2 + 170  pcs
      COMMON /input/title,month,day,year,hour,min,sec,wida,heia,
     &fra,nol,t1,t2,t3,t4,t5,midtemp,senstvy,nlevels,junk,number
      EQUIVALENCE (TITLE,BIG(1))
      TSCALE=.05
      DELAY=2000.

c     read in frame number for transient decay calculations
c
      OPEN(unit=5,file='frame-in.dat')
      read(5,'(a12)')fname
      read(5,*)frsthot,trendhot,trstcld,trendcld
      read(5,*)thot,tclnt
      read(5,*)tlowhot,tlowcld
           read(5,*)lmhotfr,ncldfr
      close(unit=5)
c
      OPEN(unit=10,file=fname,form='unformatted')
      OPEN(unit=6,file='afout.dat')
      WRITE (0,*)frsthot,trendhot,frstcld,frendcld
      write(0,*)thot,tclnt
      WRITE (0,*)  ' READING DATA'
      READ(10,end=10) (big(I),I=1,52001700)
      close(unit=10)
10    continue
c
c     **** Swapping bytes not required if run on an INTEL machine
c
      WRITE (0,*) ' SWAPPING BYTES'
      DO I=129,166,2                       ! INTERCHANGE BYTES FOR MONTH, DAY, ..... T3
       save=BIG(I)
       BIG(I)= BIG(I+1)
       BIG(I+1)= save1
      ENDDO
      save4= BIG(155)
      BIG(155)= BIG(157)
      save1= BIG(156)
      BIG(156)= BIG(158)
      BIG(157)= save4
      BIG(158)= save1                    ! INTERCHANGE T4 BYTES
c
      nbytes=hela*wida*2+fra*166
      DO I=167,NBYTES,2                  ! INTERCHANGE BYTES FOR TEMPERATURES
       save1= BIG(I)
       BIG(I)= BIG(I+1)
       BIG(I+1)= save1
      ENDDO
c
      NIMAGE=(NBYTES-166)/2/HEIA/WIDA
      WRITE (0,*) ' IMAGE WIDTH,HEIGHT ',WIDA,HEIA,' # OF FRAMES ',NIMAGE
c
      WRITE(6,'(A8,1x,A12)')'FILENAME ',FNAME
      WRITE(6,20) TITLE
      WRITE(0,20) TITLE
20    FORMAT(1X,A132)
      WRITE(6,*)  'MONTH   ',MONTH
      WRITE(6,*)  'DAY     ',DAY
      WRITE(6,*)  'YEAR    ',YEAR
      WRITE(6,*)  'HOUR    ',HOUR
      WRITE(6,*)  'MIN     ',MIN
      WRITE(6,*)  'SEC     ',SEC
      WRITE(6,*)  'WIDTH OF FRAME ',WIDA
      WRITE(6,*)  'HEIGHT OF FRAME ',HEIA
      WRITE(6,*)  'NO. OF FRAMES  ',FRA
      WRITE(6,*)  'NO. LINES      ',NOL
      WRITE(6,*)  'ELAPSED TIME (TRIGGER TO 1ST PIXEL) - MICROSEC ',T1
      WRITE(6,*)  'DELTA PIXEL TIME - NANOSEC                     ',T2
      WRITE(6,*)  'DELTA LINE TIME - MICROSEC                     ',T3
      WRITE(6,*)  'DELTA FRAME TIME - MICROSEC                    ',T4
      WRITE(6,*)  ' IMAGE WIDTH,HEIGHT',WIDA,HEIA,' # OF FRAMES ',NIMAGE
      T1S=T1*1.E-6-0.00403    ! TIME TO FIRST PIXEL    ! JFR 11/22/94
      T2S=T2*1.E-9            ! DELTA PIXEL TIME
      T3S=T3*1.E-6            ! DELTA LINE TIME
      T4S=T4*1.E-6            ! DELTA FRAME TIME
      IF(DELAY.GT.T4S) T4S=DELAY
      WRITE(0,*) ' CONVERTING NUMBERS TO TEMPERATURES AND CALCULATING TI
     1ME '
      WRITE (6,*) 'T5,MIDTEMP,SENSTY, NLVLS',t5,midtemp,senstvy,nlevels
      DO IMAGE=1,NIMAGE
       DO I=1,HEIA
        DO J=1,WIDA
         TEMP(J,I,IMAGE)=NUMBER((IMAGE-1)*WIDA*HEIA+(I-1)*WIDA+J) *
     1                   TSCALE
         TIME(J,I,IMAGE)=T1S+(J-1)*T2S+(I-1)*T3S+(IMAGE-1)*T4S
        enddo
       enddo
      enddo
c
c     exclude pixels with temperatures less than tlow C
c
      do i=1,heia
       do j=1,wida
        incl(j,i)=1
        do image=1,nimage
         if(temp(j,i,image).lt.tlowhot)incl(j,i)=0
        enddo
       enddo
      enddo
c
c     calculates thermal response hot rise
c
      reghotmin=1.0
      reghotmax=0.0
      reghotavg=0.0
      numreghot=0
      do i=1,heia
       do j=1,heia
        alphot(i,j)=0.0
        reghot(i,j)=0.0
        if(incl(i,j).eq.1)then
         do image=frsthot,trendhot
          y(image)=alog(thot-temp(i,j,image))
          x(image)=time(i,j,image)
         enddo
         num=0
         sumxy=0.0
         sumx=0.0
         sumy=0.0
```

```
           sumx2=0.0
           sumy2=0.0
           do image=fretchot,frendhot
             num=num+1
             sumxy=sumxy+y(image)*x(image)
             sumx=sumx+x(image)
             sumy=sumy+y(image)
             sumx2=sumx2+x(image)*x(image)
             sumy2=sumy2+y(image)*y(image)
           enddo
           slopeact=(num*sumxy-sumx*sumy)/(num*sumx2-sumx*sumx)
           yint=sumy/num-slopeact*sumx/num
           sumy2=0
           do image=fretchot,frendhot
             sumy2=sumy2 + (y(image)-(yint+slopeact*x(image)))**2
           enddo
           reghot(i,j)=(1.-sumy2/(num*sumy2-sumy*sumy))
           if(reghot(i,j).lt.reghotmin)reghotmin=reghot(i,j)
           if(reghot(i,j).gt.reghotmax)reghotmax=reghot(i,j)
           reghotavg=reghotavg+reghot(i,j)
           numreghot=numreghot+1
           slphot(i,j)=-slopeact
          endif
         enddo
        enddo
        reghotavg=reghotavg/numreghot write(6,*)'REGRESS HOT MIN',reghotmin
        write(6,*)'REGRESS HOT MAX',reghotmax
        write(6,*)'REGRESS HOT AVG',reghotavg
        write(6,*)'REGRESS HOT MIN=',reghotmin
        write(6,*)'REGRESS HOT MAX',reghotmax
        write(6,*)'REGRESS HOT AVG',reghotavg
        write(6,*)'TCLAT HOT degC=',thot
        write(6,*)'TLOW HOT degC=',tlowhot
        OPEN(unit=7,file='slphot.dat')
        write(7,*)' X(IN.) Y(IN.) Slope(h-int/m*cp)1  Regress'
        do j=1,wida
          xpix=(hela-j+1)*0.01
          do j=1,hela
            ypix=(hela-j+1)*0.01
            write(7,'(2F9.4,3x,g12.6,2x,f6.4)')
     1        xpix,ypix,slphot(i,j),reghot(i,j)
          enddo
        enddo
        close(unit=7)
c
c calculate thermal response of cold decay
c
        do i=1,hela
          do j=1,wida
            incl(j,i)=1
            image=ncldtr
            if(temp(j,i,image).lt.tlowcld)incl(j,i)=0
          enddo
        enddo
        regcldmin=1.0
        regcldmax=0.0
        regcldavg=0.0
        numregcld=0
        do i=1,hela
          do j=1,wida
            slpcld(i,j)=0.0
            regcld(i,j)=0.0
```

```
            if(incl(i,j).eq.1)then
              do image=fretcld,frendcld
                y(image)=alog(temp(i,j,image)-tcint)
                x(image)=time(i,j,image)
              enddo
              num=0
              sumxy=0.0
              sumx=0.0
              sumy=0.0
              sumx2=0.0
              sumy2=0.0
              do image=fretcld,frendcld
                num=num+1
                sumxy=sumxy+y(image)*x(image)
                sumx=sumx+x(image)
                sumy=sumy+y(image)
                sumx2=sumx2+x(image)*x(image)
                sumy2=sumy2+y(image)*y(image)
              enddo
              slopeact=(num*sumxy-sumx*sumy)/(num*sumx2-sumx*sumx)
              yint=sumy/num-slopeact*sumx/num
              sumy2=0
              do image=fretcld,frendcld
                sumy2=sumy2 + (y(image)-(yint+slopeact*x(image)))**2
              enddo
              regcld(i,j)=sqrt(1.-sumy2/(num*sumy2-sumy*sumy))
              if(regcld(i,j).lt.regcldmin)regcldmin=regcld(i,j)
              if(regcld(i,j).gt.regcldmax)regcldmax=regcld(i,j)
              regcldavg=regcldavg+regcld(i,j)
              numregcld=numregcld+1
              slpcld(i,j)=-slopeact
            endif
          enddo
        enddo
        regcldavg=regcldavg/numregcld write(6,*)'REGRESS COLD MIN',regcldmin
        write(6,*)'REGRESS COLD MAX',regcldmax
        write(6,*)'REGRESS COLD AVG',regcldavg
        write(6,*)'REGRESS COLD MIN',regcldmin
        write(6,*)'REGRESS COLD MAX',regcldmax
        write(6,*)'REGRESS COLD AVG',regcldavg
        write(6,*)'TCLAT HOT degC=',tcint
        write(6,*)'TLOW CLD degC=',tlowcld
        close(6)
        OPEN(unit=7,file='slpcld.dat')
        write(7,*)' X(IN.) Y(IN.) Slope(h-int/m*cp)1  Regress'
        do j=1,wida
          xpix=j*0.01
          do j=1,hela
            ypix=(hela-j+1)*0.01
            write(7,'(2F9.4,3x,g12.6,2x,f6.4)')
     1        xpix,ypix,slpcld(i,j),regcld(i,j)
          enddo
        enddo
        close(unit=7)
        stop
        end
```

```
      DIMENSION TEMP(260,200,50),reghot(260,200),regrid(260,200)
      DIMENSION siphot(260,200),incl(260,200),x(50),y150)
      DIMENSION TIME(260,200,50),sipcld(260,200)
      DIMENSION junk(6),hhot(260,200),hcld(260,200)
      integer frsthot,frendhot,tratcld,frendcld
      CHARACTER fname*12
      INTEGER*2 junk
      INTEGER*2 MONTH,DAY,YEAR,HOUR,MIN,SEC,MID,HEI,MIDA,HEIA,
     1WID,IHEI
      INTEGER*2 FRA,NOL,T1,T2,T3,T5,MIDTEMP,SENSTVY,nlevels
      INTEGER*2 NUMBER( 2600000)     ! 2600000 = 260 x 200 x 50       pcs
      INTEGER*4 T4
      CHARACTER TITLE*128
      CHARACTER*1 BIG(52001701),savel,saves   ! 2600000 x 2 + 170     pcs
      CHARACTER*1 frsthot,frendhot,tratcld,frendcld
      COMMON /input/title,month,day,year,hour,min,sec,wida,heia,
     &fra,nol,t1,t2,t3,t4,t5,midtemp,senstvy,nlevels,junk,number
      EQUIVALENCE (TITLE,BIG(1))
      TSCALE=.05
      DELAY=2000.
      DENS=.3113
      CPM300=.099
      CPM400s=.105
      COND200=-.417/3600.
      COND400=-.521/3600.

thickness=0.02
      dist=2.88/253.
c
c     read in frame number for transient decay calculations
c
      OPEN(unit=5,file='frame-in.dat')
      read(5,'(a12)')fname
      read(5,*)frsthot,frendhot,tratcld,frendcld
      read(5,*)hhot,tcint
      read(5,*)tlowhot,tlowcld
      read(5,*)nhotfr,ncldfr
      close(unit=5)

OPEN(unit=10,file=fname,form='unformatted')
      OPEN(unit=6,file='afout.dat')
      WRITE (0,*)frsthot, frendhot,tratcld,frendcld
      write(0,*)thot,tcint
      WRITE (0,*)' READING DATA'
      READ(10,end=10) (big(I1),I=1,5200170)
      close(unit=10)
10    continue
c
c     **** Swapping bytes not required if run on an INTEL machine
c
      WRITE (0,*)' SWAPPING BYTES'
      DO I=129,166,2
        savel= BIG(I)
        BIG(I)= BIG(I+1)
        BIG(I+1)= savel
      ENDDO
      savel= BIG(155)
      BIG(155)= BIG(157)
      BIG(157)= savel
      savel= BIG(156)
      BIG(156)= BIG(158)
      BIG(158)= savel nbytes=heia*wida*2*fra+166
c
      DO I=167,NBYTES,2               ! INTERCHANGE BYTES FOR TEMPERATURES
        savel= BIG(I)
        BIG(I)= BIG(I+1)
        BIG(I+1)= savel
      ENDDO NIMAGE=(NBYTES-166)/2/HEIA/WIDA
      WRITE (0,*) ' IMAGE WIDTH,HEIGHT',WIDA,HEIA,' # OF FRAMES ',NIMAGE
c
      WRITE(6,'(A8,1X,A12)')'FILENAME ',FNAME
      WRITE(6,20) TITLE
      WRITE(0,20) TITLE
20    FORMAT(1X,A132)
      WRITE(6,*) 'MONTH    ',MONTH
      WRITE(6,*) 'DAY      ',DAY
      WRITE(6,*) 'YEAR     ',YEAR
      WRITE(6,*) 'HOUR     ',HOUR
      WRITE(6,*) 'MIN      ',MIN
      WRITE(6,*) 'SEC      ',SEC
      WRITE(6,*) 'WIDTH OF FRAME  ',WIDA
      WRITE(6,*) 'HEIGHT OF FRAME ',HEIA
      WRITE(6,*) 'NO. OF FRAMES   ',FRA
      WRITE(6,*) 'NO. LINES       ',NOL
      WRITE(6,*) 'ELAPSED TIME (TRIGGER TO 1ST PIXEL) - MICROSEC ',T1
      WRITE(6,*) 'DELTA PIXEL TIME - NANOSEC       ',T2
      WRITE(6,*) 'DELTA LINE TIME - MICROSEC       ',T3
      WRITE(6,*) 'DELTA FRAME TIME - MICROSEC      ',T4
      WRITE(6,*) ' IMAGE WIDTH,HEIGHT',WIDA,HEIA,' # OF FRAMES ',NIMAGE
      T1S=T1*1.E-6+0.00403  ! TIME TO FIRST PIXEL     ! JFR 11/22/94
      T2S=T2*1.E-9          ! DELTA PIXEL TIME
      T3S=T3*1.E-6          ! DELTA LINE TIME
      T4S=T4*1.E-6          ! DELTA FRAME TIME
      IF(DELAY.GT.T4S) T4S=DELAY
      WRITE(0,*)' CONVERTING NUMBERS TO TEMPERATURES AND CALCULATING TI
     1ME'
      WRITE (6,*)'T5,MIDTEMP,SENSTY,NLVLS',t5,midtemp,senstvy,nlevels
      DO IMAGE=1,NIMAGE
      DO I=1,HEIA
      DO J=1,WIDA
        TEMP(J,I,IMAGE)=NUMBER((IMAGE-1)*WIDA*HEIA+(I-1)*WIDA+J) *
     1                 TSCALE*1.8+12.
        TIME(J,I,IMAGE)=T1S+(J-1)*T2S+(I-1)*T3S+(IMAGE-1)*T4S
      enddo
      enddo
      enddo
c
c     exclude pixels with temperatures less than tlow C
c
      do i=1,heia
        do j=1,wida
          incl(j,i)=1
          imageenhotfr
          if(temp(j,i,image).lt.tlowhot)incl(j,i)=0
        enddo
      enddo
c
c     calculate thermal response hot rise
c
      reghotmin=1.0
      reghotmax=0.0
      reghotavg=0.0
      numreghot=0
      do i=1,heia
        siphot(i,j)=0.0
        reghot(i,j)=0.0
        if(incl(i,j).eq.1) then
```

```
          num=0
          sumxy=0.0
          sumx=0.0
          sumy=0.0
          sumx2=0.0
          sumy2=0.0
          do image=fstchot,trendhot
            y(image)=alog(thot-temp(i,j,image))
            x(image)=time(i,j,image)
            sumxy=sumxy+y(image)*x(image)
            num=num+1
            sumx=sumx+x(image)
            sumy=sumy+y(image)
            sumx2=sumx2+x(image)*x(image)
            sumy2=sumy2+y(image)*y(image)
          enddo
          slopeact=(num*sumxy-sumx*sumy)/(num*sumx2-sumx*sumx)
          yint=sumy/num-slopeact*sumx/num
          sumy2=0
          do image=fstchot,trendhot
            sumy2=sumy2 + (y(image)-(yint+slopeact*x(image)))**2
          enddo
          reghot(i,j)=(1.-sumy2/(num*sumy*sumy))
          if(reghot(i,j).lt.reghotmin) reghotmin=reghot(i,j)
          if(reghot(i,j).gt.reghotmax) reghotmax=reghot(i,j)
          reghotavg=reghotavg+reghot(i,j)
          numreghot=numreghot+1
          slphot(i,j)=-slopeact
          havg=0
          do image=fstchot,trendhot-1
            cpm=cpm200+(temp(i,j,image)-200.)*(cpm400-cpm200)/200.
            condm=cond200+(temp(i,j,image)-200.)*(cond400-cond200)/200.
            h=thickness/(thot-temp(i,j,image))*(dens*cpm*(temp(i,
     1     j,image+1)-temp(i,j,image))/(time(i,j,image+1)-time(
     1     i,j,image))-condm/disc**2*(incl(i+1,j,image)+incl(i-1,j,image)
     1     +incl(i,j-1,image)+incl(i,j+1,image)-4*incl(i,j)+
     1     incl(i-1,j)+incl(i+1,j)+incl(i,j-1)+incl(i,j+1))*temp(i,j,image))
            hhot(i,j)=havg/((trendhot-1-fstchot))
          enddo
          endif
        enddo
      enddo
      reghotavg=reghotavg/numreghot write(0,*)'REGRESS HOT MIN',reghotmin
      write(0,*)'REGRESS HOT MAX',reghotmax
      write(0,*)'REGRESS HOT AVG',reghotavg
      write(6,*)'REGRESS HOT MIN=',reghotmin
      write(6,*)'REGRESS HOT MAX=',reghotmax
      write(6,*)'REGRESS HOT AVG=',reghotavg
      write(6,*)'TCLNT HOT degc=',tchot
      write(6,*)'TLOW HOT degc=',tlowhot
      OPEN(unit=7,file='slphot.dat')
      write(7,*)' X(IN.) Y(IN.) Slope(h-int/m*cp)1 Regress'
      do i=1,wida
        do j=1,hela
          if(incl(i,j).eq.1)then
            ypix=(hela-j+1)*0.01
            write(7,'(2F9.4,3x,g12.6,2x,f6.4,2x,g12.6)')
     1       xpix,ypix,slphot(i,j),reghot(i,j),hhot(i,j)
```

```
          endif
        enddo
      enddo
      close(unit=7)

c     calculate thermal response of cold decay do i=1,hela
        do j=1,wida
          incl(j,1)=1
          image=ncldtr
          if(temp(j,i,image).lt.tlowcld)incl(j,i)=0
        enddo
      enddo
      regcldmin=1.0
      regcldmax=0.0
      regcldavg=0.0
      numregcld=0
      do j=1,hela
        slpcld(i,j)=0.0
        regcld(i,j)=0.0
        if(incl(i,j).eq.1)then
          do image=fstcld,trendcld
            y(image)=alog(temp(i,j,image)-tclnt)
            x(image)=time(i,j,image)
          enddo
          num=0
          sumxy=0.0
          sumx=0.0
          sumy=0.0
          sumx2=0.0
          sumy2=0.0
          do image=fstcld,trendcld
            sumxy=sumxy+y(image)*x(image)
            num=num+1
            sumx=sumx+x(image)
            sumy=sumy+y(image)
            sumx2=sumx2+x(image)*x(image)
            sumy2=sumy2+y(image)*y(image)
          enddo
          slopeact=(num*sumxy-sumx*sumy)/(num*sumx2-sumx*sumx)
          yint=sumy/num-slopeact*sumx/num
          sumy2=0
          do image=fstcld,trendcld
            sumy2=sumy2 + (y(image)-(yint+slopeact*x(image)))**2
          enddo
          regcld(i,j)=sqrt(1.-sumy2/(num*sumy*sumy))
          if(regcld(i,j).lt.regcldmin)regcldmin=regcld(i,j)
          if(regcld(i,j).gt.regcldmax)regcldmax=regcld(i,j)
          regcldavg=regcldavg+regcld(i,j)
          numregcld=numregcld+1
          slpcld(i,j)=-slopeact
        endif
      enddo
      regcldavg=regcldavg/numregcld
      write(0,*)'REGRESS COLD MIN',regcldmin
      write(0,*)'REGRESS COLD MAX',regcldmax
      write(0,*)'REGRESS COLD AVG',regcldavg
      write(6,*)'REGRESS COLD MIN',regcldmin
      write(6,*)'REGRESS COLD MAX',regcldmax
      write(6,*)'REGRESS COLD AVG',regcldavg
```

```
        write(6,*)'TCLNT degCe',tclnt
        write(6,*)'TLOW CLD degCe',tlowcld
        close(6)
        OPEN(unit=7,file='slpcld.dat')
write(7,*)' X(IN.) Y(IN.) Slope(h-int/m*cp)1 Regress'
        do i=1,wida
          xpix=i*0.01
    do j=1,hela
          ypix=(hela-j+1)*0.01
        write(7,'(2F9.4,3x,g12.6,2x,f6.4)')
1       xpix,ypix,slpcld(i,j),regcld(i,j)
    enddo
        enddo
        close(unit=7)
        stop
        end
```

FIG. 27

```
      DIMENSION TEMP(260,200,50),reghot(260,200),regold(260,200)
      DIMENSION siphot(260,200),lncl(260,200),x(50),y(50),h(50)
      DIMENSION TIME(260,200,50),slpcld(260,200),hcld(260,200)
      DIMENSION junk(6),hhot(260,200),hcld(260,200)
      dimension qrathot(260,200),qrstcld(260,200),hvarmax(260,200)
      integer frshot,frcold,frendhot,frstcld,trendcld
      CHARACTER fname*12
      INTEGER*2 junk
      INTEGER*2 MONTH,DAY,YEAR,HOUR,MIN,SEC,MID,HEI,MIDA,HEIA,
     &          MID,IHEI
      INTEGER*2 FRA,NOL,T1,T2,T3,T5,MIDTEMP,SENSTVY,nlevels
      INTEGER*2 NUMBER( 2600000)    ! 2600000 = 260 x 200 x 50      pcs
      INTEGER*4 T4
      CHARACTER TITLE*132                                            pcs
      CHARACTER*1 BIG(5200170),savel,saves    ! 2600000 x 2 + 170
      COMMON /input/title,month,day,year,hour,min,sec,wida,heia,
     &fra,nol,t1,t2,t3,t4,t5,midtemp,senstvy,nlevels,junk,number
      EQUIVALENCE (TITLE,BIG(1))
      TSCALE=.05
      DELAY=2000.
      DENS=.3113
      CPM200=.099
      CPM400=.105
      COND200=.417/3600.
      COND400=.521/3600.
      thickness=0.02
      disc=2.88/253.
c
c     read in frame number for transient decay calculations
c
      OPEN(unit=5,file='frame-in.dat')
      read(5,'(a12)')fname
      read(5,*)frshot,frendhot,frstcld,frendcld
      read(5,*)thot,tcint
      read(5,*)tlowhot,tlowcld
      read(5,*)nhotfr,ncldfr
      close(unit=5)
c
      OPEN(unit=10,file=fname,form='binary')
      OPEN(unit=6,file='afout.dat')
      WRITE (0,*)frshot,frendhot,frstcld,frendcld
      write(0,*)thot,tcint
      WRITE (0,*)' READING DATA'
      READ(10,end=10) (big(i),i=1,5200170)
      close(unit=10)
c
c**** Swapping bytes not required if run on an INTEL machine
c
      WRITE (0,*)' SWAPPING BYTES'
      DO I=129,166,2
         savel= BIG(I)
         BIG(I)= BIG(I+1)
         BIG(I+1)= savel
      ENDDO
      BIG(155)= BIG(157)
      BIG(157)= savel
      savel= BIG(156)
      BIG(156)= BIG(158)
      BIG(158)= savel
                                  ! INTERCHANGE BYTES FOR MONTH, DAY, .... T3
                                  ! INTERCHANGE T4 BYTES
      nbytes=heia*wida*2+fra+170
      DO I=167,NBYTES,2           ! INTERCHANGE BYTES FOR TEMPERATURES
         savel= BIG(I)
```

```
         BIG(I)= BIG(I+1)
         BIG(I+1)= savel
      ENDDO
c
      NIMAGE=(NBYTES-170)/2/HEIA/WIDA
      WRITE (0,*) ' IMAGE WIDTH,HEIGHT,WIDA,HEIA, # OF FRAMES ',NIMAGE
c
      WRITE(6,'(A8,1x,A12)')'FILENAME ',FNAME
      WRITE(6,20) TITLE
      WRITE(0,20) TITLE
   20 FORMAT(1X,A132)
      WRITE(6,*) 'MONTH  ',MONTH
      WRITE(6,*) 'DAY    ',DAY
      WRITE(6,*) 'YEAR   ',YEAR
      WRITE(6,*) 'HOUR   ',HOUR
      WRITE(6,*) 'MIN    ',MIN
      WRITE(6,*) 'SEC    ',SEC
      WRITE(6,*) 'WIDTH OF FRAME   ',WIDA
      WRITE(6,*) 'HEIGHT OF FRAME  ',HEIA
      WRITE(6,*) 'NO. OF FRAMES    ',FRA
      WRITE(6,*) 'NO. LINES        ',NOL
      WRITE(6,*) 'ELAPSED TIME (TRIGGER TO 1ST PIXEL) - MICROSEC ',T1
      WRITE(6,*) 'DELTA PIXEL TIME - NANOSEC ',T2
      WRITE(6,*) 'DELTA LINE TIME  - MICROSEC',T3
      WRITE(6,*) 'DELTA FRAME TIME - MICROSEC',T4
      WRITE(6,*) ' IMAGE WIDTH,HEIGHT,WIDA,HEIA, # OF FRAMES ',NIMAGE
      T1S=T1*1.E-6+0.00403   ! TIME TO FIRST PIXEL   ! JFR 11/22/94
      T2S=T2*1.E-9           ! DELTA PIXEL TIME
      T3S=T3*1.E-6           ! DELTA LINE TIME
      T4S=T4*1.E-6           ! DELTA FRAME TIME
      IF(DELAY.GT.T4S) T4S=DELAY
      WRITE(0,*)' CONVERTING NUMBERS TO TEMPERATURES AND CALCULATING TI
     1ME'
      WRITE (6,*)T1,T5,MIDTEMP,SENSTY,NUVLS',t5,midtemp,senstvy,nlevels
      DO IMAGE=1,NIMAGE
         DO J=1,HEIA
            DO I=1,WIDA
               TEMP(J,I,IMAGE)=NUMBER((IMAGE-1)*WIDA*HEIA+(I-1)*WIDA+J)
     &                         TSCALE*1.8+32.
               TIME(J,I,IMAGE)=T1S+(J-1)*T2S+(I-1)*T3S+(IMAGE-1)*T4S
            enddo
         enddo
      enddo
c
c     exclude pixels with temperatures less than tlow C
c
      do i=1,heia
         do j=1,wida
            incl(j,i)=1
            if(temp(j,i,image).lt.tlowhot)then
               image=nhotfr
               incl(j,i)=0
            endif
         enddo
      enddo
c
c     calculate thermal response hot rise
c
      reghotmin=1.0
      reghotmax=0.0
      reghotavg=0.0
      numreghot=0
      do i=1,wida
```

```
            do j=1,hela
                alphot(i,j)=0.0
                reghot(i,j)=0.0
                if(inci(i,j).eq.1)then
                    num=0
                    sumxy=0.0
                    sumx=0.0
                    sumy=0.0
                    sumx2=0.0
                    sumy2=0.0
                    do image=frsthot,trendhot
                        y(image)=-alog(thot-temp(i,j,image))
                        x(image)=time(i,j,image)
                        numenum-1
                        sumxy=sumxy+y(image)*x(image)
                        sumx=sumx+x(image)
                        sumy=sumy+y(image)
                        sumx2=sumx2+x(image)*x(image)
                        sumy2=sumy2+y(image)*y(image)
                    enddo
                    slopeact=(num*sumxy-sumx*sumy)/(num*sumx2-sumx*sumx)
                    yintesumy/num-slopeact*sumx/num
                    sumry2=0
                    do image=frsthot,trendhot
                        sumry2=sumry2 + (y(image)-(yint-slopeact*x(image)))**2
                    enddo
                    reghot(i,j)=sqrt((1.-sumry2/(num*sumy2-sumy*sumy))
                    if(reghot(i,j).lt.reghotmin)reghotmin=reghot(i,j)
                    if(reghot(i,j).gt.reghotmax)reghotmax=reghot(i,j)
                    reghotavg=reghotavg+reghot(i,j)
                    numreghot=numreghot+1
                    alphot(i,j)=slopeact
                    qconavg=0
                    qcondavg=0
                    havg=0
                    do image=frsthot,trendhot
                        havg=havg+h(image)
                        cpm=cpm200+(temp(i,j,image)-200.)*(cpm400-cpm200)/200.
                        condm=cond200+(temp(i,j,image)-200.)*(cond400-cond200)/
           200.
                        h(image)=thickness/(thot-temp(i,j,image))*(degs*cpm*cpm*(temp(
        1           i,j,image+1)-temp(i,j,image))/(time(i,j,image+1)-time(
        1           i,j,image))-condm/dist**2*(inci(i+1,j,image)
        1           +inci(i-1,j)*temp(i-1,j,image)+inci(i,j+1)*temp(i,j+1,
                    image)+inci(i,j-1)*temp(i,j-1,image)-(inci(i+1,j)+
                    inci(i-1,j)+inci(i,j+1)+inci(i,j-1))*temp(i,j,image)))
                    h(image)=h(image)*3600.*144.
                    write(*,*)i,j,h(image)
                    havg=havg+h(image)
                    qconvh(image)=dist**2*(thot-temp(i,j,image))/1144./3600.
                    qcond=cond*thickness*(inci(i+1,j)*temp(i+1,j,image)
        1           +inci(i-1,j)*temp(i-1,j,image)+inci(i,j+1)*temp(i,j+1,
                    image)+inci(i,j-1)*temp(i,j-1,image)-(inci(i+1,j)+
        1           inci(i-1,j)+inci(i,j+1)+inci(i,j-1))*temp(i,j,image))
                    qconavg=qconavg+qcond
                    qcondavg=qcondavg+qcond
                    enddo
                    hhot(i,j)=havg/(trendhot-1-frsthot)
                    qrathot(i,j)=qconavg/abs(qcondavg)
                    hvarmax(i,j)=0.0
                    do image=frsthot,trendhot
                        if(abs(h(image)-hhot(i,j)).gt.hvarmax(i,j))
        1               hvarmax(i,j)=abs(h(image)-hhot(i,j))
                    enddo
                    if(hhot(i,j).lt.0.0)inci(i,j)=0
                endif
            enddo
        enddo
        reghotavg=reghotavg/numreghot
        write(0,*)'REGRESS HOT MIN',reghotmin
        write(0,*)'REGRESS HOT MAX',reghotmax
        write(0,*)'REGRESS HOT AVG',reghotavg
        write(6,*)'REGRESS HOT MIN',reghotmin
        write(6,*)'REGRESS HOT MAX',reghotmax
        write(6,*)'REGRESS HOT AVG',reghotavg
        write(6,*)'TCLAT HOT degC',thot
        write(6,*)'TLOW HOT degC',tlowhot
        OPEN(unit=7,file='alphot.dat')
        write(7,*)' X(IN.) Y(IN.) Slope(h-int/m*cp)1 Regress'
        do i=1,wida
            do j=1,hela
                if(inci(i,j).eq.1)then
                    ypix=(hela-j+1)*dist
                    xpix=i*dist
                    write(7,'(2F9.4,3x,g12.6,2x,f6.4,2x,f8.3)')
        1           xpix,ypix,alphot(i,j),reghot(i,j),hhot(i,j)
                endif
            enddo
        enddo
        close(unit=7)
        OPEN(unit=7,file='qnvhot.dat')
        write(7,*)' X(IN.) Y(IN.) ConvRatio. HvarMax'
        do i=1,wida
            xpix=i*dist
            do j=1,hela
                if(inci(i,j).eq.1)then
                    ypix=(hela-j+1)*dist
                    write(7,'(2F9.4,3x,f6.4,2x,f8.3)')
        1           xpix,ypix,qrathot(i,j),hvarmax(i,j)
                endif
            enddo
        enddo
        close(unit=7)
c
c       calculate thermal response of cold decay
c
        do j=1,hela
            do i=1,wida
                inclh(i,j)=1
                inclh(j,i)=1
                imagesncldfr
                if(temp(j,i,image).lt.tlowcld)then
                    inci(j,i)=0
                endif
            enddo
        enddo
        do i=1,wida
            do j=1,hela
                alpcld(i,j)=0.0
                regcldmin=1.0
                regcldmax=0.0
                regcldavg=0.0
                numregcld=0
                do j=1,hela
                    if(inci(i,j).eq.1)then
                        num=0
                        sumxy=0.0
                        sumx=0
```

```
sumy=0.0
sumx2=0.0
sumy2=0.0
do image=tratcold,trendcold
  y(image)=alog(temp(i,j,image)-tcint)
  x(image)=time(i,j,image)
  numenum+1
  sumxy=sumxy+y(image)*x(image)
  sumx=sumx+x(image)
  sumy=sumy+y(image)
  sumx2=sumx2+x(image)*x(image)
  sumy2=sumy2+y(image)*y(image)
enddo
slopeact=(num*sumxy-sumx*sumy)/(num*sumx2-sumx*sumx)
yint=sumy/num-slopeact*sumx/num
sumy2=0
do image=tratcold,trendcold
  sumy2=sumy2 + (y(image)-(yint+slopeact*x(image)))**2
enddo
regcld(i,j)=sqrt((..sumy2/(num*sumy2-sumy*sumy))
if((regcld(i,j).lt.regcldmin)regcldmin=regcld(i,j)
if((regcld(i,j).gt.regcldmax)regcldmax=regcld(i,j)
regcldavg=regcldavg+regcld(i,j)
numregcld=numregcld+1
slpcld(i,j)=-slopeact
havg=0.0
do image=tratcold,trendcold-1
  cpm=cpm200+(temp(i,j,image)-200.)*(cpm400-cpm200)/200.
  condm=cond200+(temp(i,j,image)-200.)*(cond400-cond200)/200.
  h(image)=thickness/(tcint-temp(i,j,image))*(dens*cpm*(temp
  (i,j,image+1)-temp(i,j,image))/(time(i,j,image+1)-time(
  i,j,image))-condm/disc**2*(incl(i-1,j,image)+incl(i+1,j,image)
  +incl(i-1,j)*temp(i-1,j,image)+incl(i,j-1)*temp(i,j-1,
  image)+incl(i,j+1)*temp(i,j+1,image)-(incl(i-1,j)+
  incl(i-1,j)+incl(i,j+1)+incl(i,j-1))*temp(i,j,image)))
  havg=havg+h(image)*3600.
enddo
hcld(i,j)=havg/((trendcold-1-tratcold)*144.
if(hcld(i,j).lt.0.0)incl(i,j)=0
endif
@enddo
@Vendo enddo
c    w regcldavg=regcldavg/numregcld
     regcldavg = regcldavg/numregcld
write(6,*)'REGRESS COLD MIN',regcldmin
write(6,*)'REGRESS COLD MAX',regcldmax
write(6,*)'REGRESS COLD AVG',regcldavg
write(6,*)'REGRESS COLD MIN',regcldmin
write(6,*)'REGRESS COLD MAX',regcldmax
write(6,*)'REGRESS COLD AVG',regcldavg
write(6,*)'TCLNT degC',tcint
write(6,*)'TLOW CLD degC',tlowcld
close(6)
OPEN(unit=7,file='slpcld.dat')
write(7,*)' ',X(IN.) Y(IN.) Slope(h-int/m*cp)1  Regress'
do i=1,wide
  xpix=i*dist
  do j=1,hei
    if(incl(i,j).eq.1)then
      ypix=(hei+1-j+1)*dist
      write(7,'(2f9.4,3x,g12.6,2x,f6.4,2x,f8.3)')
      xpix,ypix,slpcld(i,j),regcld(i,j),hcld(i,j)
    endif
  enddo
enddo
close(unit=7)
stop
end
```

What is claimed is:

1. A method, comprising:

providing a component having an internal passage adapted for the passage of a cooling media;

heating the component;

flowing the cooling media through the internal passage after said heating;

evaluating the surface of the component with an infrared thermal imaging device during said heating and flowing;

acquiring transient surface temperature data of the component in a pixel format by using the infrared thermal imaging device;

converting the transient surface temperature data into a processing data format including time, temperature, and x,y location;

processing the processing data in a transient heat balance equation to obtain convective heat transfer coefficients for each pixel and time increment; and time averaging the heat transfer coefficients for each pixel.

2. The method of claim 1, which further includes comparing the heat transfer coefficients with a predetermined set of heat transfer coefficients.

3. The method of claim 1, wherein in said acquiring the transient surface temperature data is stored in a binary digital format.

4. The method of claim 1, wherein said heating is defined by heat being applied through an outer surface of the component.

5. The method of claim 1, wherein said evaluating is done by dividing the surface of the component into pixel control volumes having a size within a range of about 0.010 square inches to about 0.025 square inches.

6. The method of claim 1, wherein in said evaluating the surface of the component is divided into pixel control volumes, and wherein in said processing the transient heat balance equation considers heat transfer from the pixel control volume to the cooling media flowing through the internal passage, energy storage within a first pixel control volume, and conduction to and from four pixel control volumes adjacent to the first pixel control volume.

7. The method of claim 6, wherein in said processing the thickness of each pixel control volume is assumed to be evenly distributed in solving the transient heat balance equation.

8. The method of claim 6, wherein in said processing the actual thickness of each control volume is known and used to solve the transient heat balance equation.

9. The method of claim 1, wherein in said processing the transient heat balance equation is defined by $\rho C_p t_h \Delta x^2 \Delta T_{m,t}/\Delta t = h\Delta x^2(T_m-T_c)+k_m \Delta x\, t_h \Sigma(\Delta T_{m,xl}/\Delta x)$.

10. The method of claim 1, which further includes separating the convective heat transfer component from the conductive heat transfer component.

11. The method of claim 1, which further includes comparing the heat transfer coefficients with a predetermined set of heat transfer coefficients; wherein said heating is defined by the heat being applied through an outer surface of the component; and, wherein in said evaluating the surface of the component is divided into pixel control volumes, and further wherein in said processing the transient heat balance equation considers heat transfer from the pixel control volume to the cooling media flowing through the internal passage, energy storage within a first pixel control volume, and conduction to and from four pixel control volumes adjacent to the first pixel control volume.

12. A method for the heat transfer inspection of an internally cooled component at near ambient conditions, comprising:

providing a component having an internal passage adapted for the passage of a cooling media;

heating the component;

flowing the cooling media through the internal passage after said heating;

evaluating the surface of the component with an infrared thermal imaging device during said heating and flowing;

acquiring transient surface temperature data of the component in a pixel format by using the infrared thermal imaging device; and processing the transient surface temperature data of the component in a transient heat balance equation to yield a convective heat transfer coefficient for each pixel.

13. The method of claim 12, wherein in said providing the component is formed of a super alloy material, and which further includes comparing the heat transfer coefficient for each pixel with at least one predetermined heat transfer coefficient.

14. The method of claim 12, wherein in said acquiring the transient surface temperature data is stored in a binary digital format, and wherein said heating is defined by heat being applied through an outer surface of the component.

15. The method of claim 12, wherein said evaluating includes dividing the surface of the component into a plurality of pixel control volumes having a size within a range of about 0.010 square inches to about 0.025 square inches.

16. The method of claim 12, wherein in said processing the transient heat balance equation is defined by $\rho C_p t_h \Delta x^2 \Delta T_{m,t}/\Delta t = h\Delta x^2(T_m-T_c)+k_m \Delta x t_h \Sigma(\Delta T_{m,x}/\Delta x)$.

17. The method of claim 12, which further includes comparing the heat transfer coefficient of each pixel with a predetermined set of heat transfer coefficients; wherein said heating is defined by heat being applied through an outer surface of the component; and, wherein in said evaluating the surface of the component is divided into pixel control volumes, and further wherein in said processing the transient heat balance equation considers heat transfer from the pixel control volume to the cooling media flowing through the internal passage, energy storage within a first pixel control volume, and conduction to and from four pixel control volumes adjacent to the first pixel control volume.

18. A method for the heat transfer inspection of an internally cooled component at near ambient conditions, comprising:

providing a component having an internal passage adapted for the passage of a cooling media;

heating the component;

flowing the cooling media through the internal passage after said heating;

dividing the surface of the component into a plurality of control volumes;

evaluating each of the plurality of control volumes defining the surface of the component with an infrared thermal imaging device during said heating and said flowing;

acquiring transient surface temperature data of the component in a pixel format by using the infrared thermal imaging device; and processing the transient surface temperature data of the component in a transient heat balance equation to yield a convective heat transfer characteristic for each pixel separate from a conductive heat transfer characteristic for each pixel.

* * * * *

UNITED STATES PATENT AND TRADEMARK OFFICE
CERTIFICATE OF CORRECTION

PATENT NO. : 6,422,743 B1
DATED : July 23, 2002
INVENTOR(S) : Nirm V. Nirmalan et al.

It is certified that error appears in the above-identified patent and that said Letters Patent is hereby corrected as shown below:

<u>Column 6,</u>
Line 11, please change formula to read,

-- $\rho C_p t_h (T_{m:i, j, n+1} - T_{m:i,j,n})/(t_{i, j, n+1} - t_{i,j,n}) = h(t_{m:i, j, n} - T_{c:i}) +$ $k(T_{m:i,j,n} - T_{m:i-1,j,n}) t_h / \Delta x^2 + (T_{m:i,j,n} - T_{m:i+1,j,n}) t_h \Delta x^2 + k(T_{m:i,j,n} - T_{m:i-1,j,n}) t_h /$ $\Delta x^2 + k(T_{m:i,j,n} - T_{m:i+1,j,n}) t^h / \Delta x^2$ --

<u>Column 41,</u>
Lines 54-55, please change formula to read,

-- $\rho C_p t_h \Delta x^2 \Delta T_{m,t} / \Delta t = h \Delta x^2 (T_m - T_c) + k_m \Delta x t_h \Sigma (\Delta T_{m,x} / \Delta x)$. --

Signed and Sealed this

Third Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,422,743 B1
DATED : July 23, 2002
INVENTOR(S) : Nirm V. Nirmalan et al.

It is certified that error appears in the above-identified patent and that said Letters Patent is hereby corrected as shown below:

<u>Column 6,</u>
Line 11, please change formula to read,

-- $\rho C_p t_h(T_{m:i,j,n+1}-T_{m:i,j,n})/(t_{i,j,n+1}-t_{i,j,n})=h(T_{m:i,j,n}-T_{c:i})+$ $k(T_{m:i,j,n}-T_{m:i-1,j,n})t_h/\Delta x^2+(T_{m:i,j,n}-T_{m:i+1,j,n})t_h \Delta x^2+k(T_{m:i,j,n}-T_{m:i-1,j,n})t_h/$ $\Delta x^2+k(T_{m:i,j,n}-T_{m:i+1,j,n})t^h/\Delta x^2$ --

<u>Column 41,</u>
Lines 54-55, please change formula to read,

-- $\rho C_p t_h \Delta x^2 \Delta T_{m,t}/\Delta t = h\Delta x^2(T_m-T_c)+k_m\Delta x t_h \Sigma(\Delta T_{m,x}/\Delta x).$ --

This certificate supersedes Certificate of Correction issued December 3, 2002.

Signed and Sealed this

Eighteenth Day of November, 2002

JAMES E. ROGAN
*Director of the United States Patent and Trademark Office*